United States Patent [19]
Uriach-Marsal et al.

[11] Patent Number: 5,932,438
[45] Date of Patent: Aug. 3, 1999

[54] PREPARATION OF THAUMATIN SWEETENERS

[75] Inventors: Juan Uriach-Marsal, Barcelona; Victor Rubio-Susan, Madrid; Cristina Patiño-Martin, Madrid; Eliza Iossif Kalo-Koenova, Madrid; Catalina del Moral-Juarez, Madrid; Ignacio Faus-Santasusana, Barcelona; Jose-Luis del Rio-Pericacho, Terrasa; Joan Blade-Pique, Barcelona, all of Spain

[73] Assignee: Urquima, S.A., Spain

[21] Appl. No.: 08/426,599

[22] Filed: Apr. 21, 1995

[30] Foreign Application Priority Data

Apr. 21, 1994 [ES] Spain ...................................... 9400836

[51] Int. Cl.$^6$ ............................. C12P 21/06; C12P 21/04; C07H 21/02; C07H 21/04
[52] U.S. Cl. ....................... 435/69.1; 435/69.7; 435/70.1; 435/254.3; 435/254.5; 435/320.1; 536/23.1; 536/23.4; 536/23.74; 935/22
[58] Field of Search .................................. 435/69.1, 69.7, 435/70.1, 71.1, 254.3, 254.5, 320.1; 536/23.1, 23.4, 23.74; 935/22

[56] References Cited

U.S. PATENT DOCUMENTS

| | | | |
|---|---|---|---|
| 4,771,000 | 9/1988 | Verrips et al. | 435/70 |
| 4,891,316 | 1/1990 | Verrips et al. | 435/69.1 |
| 5,221,624 | 6/1993 | Blair et al. | 435/252.33 |

FOREIGN PATENT DOCUMENTS

| | | |
|---|---|---|
| 0054330 | 6/1982 | European Pat. Off. . |
| 0054331 | 6/1982 | European Pat. Off. . |
| 0096430 | 12/1983 | European Pat. Off. . |
| 0096910 | 12/1983 | European Pat. Off. . |
| 0139501 A3 | 5/1985 | European Pat. Off. . |
| 2200118 | 7/1988 | United Kingdom . |
| 83/04051 | 11/1983 | WIPO . |
| 86/06097 | 10/1986 | WIPO . |
| 03007 | 5/1987 | WIPO . |
| 8703007 | 5/1987 | WIPO . |
| 06283 | 7/1989 | WIPO . |
| 90/05775 | 5/1990 | WIPO . |

OTHER PUBLICATIONS

Makrides (1996) Strategies for achieving high–level expression of genes in *Escherichia coli.* Microbiological Reviews 60(3): 512–538, Sep. 1996.

Gouka et al. (1997) Efficient production of secreted proteins by Aspergillus: progress, limitations and prospects. Appl. Microbiol. Biotechnol. pp. 1–11, Jan. 1997.

Edens et al. (1982) Cloning of cDNA encoding the sweet-tasting plant protein thaumatin and its expression in *Escherichia coli*, Gene 18: 1–12, Jan. 1982.

Hahm et al. (1990) Expression and Secretion of Thaumatin from *Aspergillus oryzae*, Agric. Biol. Chem. 54 (10): 2513–2520, Jan. 1990.

Lloyd et al. (1991) Codon usage in *Aspergillus nidulans*. Molecular and General Genetics 230(1–2): 288–294, Nov. 1991.

Hahm, Y.T., et al., *Agric. Biol. Chem.*, vol. 54(10) (1990), 2513–2520.

Witty, M., et al., *New Zealand Journal of Crop and Horticultural Science*, vol. 18 (1990), 77–80.

Y.T. Hahm et al., *Agric. Biol. Chem.*, vol. 54(10) (1990), pp. 2513–2520.

J.H. Lee et al., *Biochemistry*, vol. 27(14) (1988), pp. 5101–5107.

A.T. Lloyd et al., *Mol. Gen. Genet.*, vol. 230 (1991), pp. 288–294.

European Search Report dated Jun. 14, 1996 for related patent application EP 95105973.2 (1996).

*Primary Examiner*—Robert A. Wax
*Assistant Examiner*—Einar Stole
*Attorney, Agent, or Firm*—Rothwell, Figg, Ernst & Kurz, P.C.

[57] ABSTRACT

Thaumatins, protein sweeteners, are obtained through the expression of artificial, synthetic and substantially optimized genes, preferably in filamentous fungi such as *Penicillium roquefortii, Aspergillus niger* and *Aspergillus niger* var. *awamori*. Preparing substantially optimized artificial genes allows for high protein expression, making the process useful for industrial production of this valuable sweetener. Thaumatins may be obtained extracellularly and intracellularly. Intracellular production provides thaumatin-containing fungi that can be used per se in animal feed without prior separation of the fungal mycelium.

30 Claims, 15 Drawing Sheets

FIG. 1A

```
        272                                          304
         ↘                                            ↘
5'-....CCCGGGGATCCTCTAGAGTCGACCTGCAGGCAT....-3'
3'-....GGGCCCCTAGGAGATCTCAGCTGGACGTCCGTA....-5'
              BamHI                  PstI
```

FIG. 1B

```
5'-....CCCGGGGATCCTCTCCATGGGACCTGCAGGCAT....-3'
3'-....GGGCCCCTAGGAGAGGTACCCTGGACGTCCGTA....-5'
              BamHI     NcoI        PstI
```

(106 NUCLEOTIDES).
5'-AAATGGAGGATCCATGGCCACCTTCGAGATCGTCAACCGC
TGCTCCTACACCGTCTGGGCCGCCGCCTCCAAGGGCGACGC
CGCCCTCGACGCCGGCGGCCGCCAG-3'

FIG. 3A (87 NUCLEOTIDES).
5'-GCGGGCCCAGATCTTGCCGCCCTTGGTGCCGGGCTCGAC
GTTGATGGTCCAGGACTCGCCGGAGTTGAGCTGGCGGCCGC
CGGCGTC-3'

FIG. 3B (117 NUCLEOTIDES).
5'-GGCGGCAAGATCTGGCCCGCACCGACTGCTACTTCGACG
ACTCCGGCCGCGGCATCTGCCGCACCGGCGACTGCGGCGGC
CTCCTCCAGTGCAAGCGCTTCGGCCGCCCCCCCACC-3'

FIG. 3C (103 NUCLEOTIDES).
5'-AGTCCATGGGGACGTTGAAGCCCTTGATGTTGGAGATGTCG
ATGTAGTCCTTGCCGTACTGGTTGAGGGAGAACTCGGCGAGGG
TGGTGGGGGGCGGCCGAA-3'

FIG. 3D (84 NUCLEOTIDES).
5'-AACGTCCCCATGGACTTCTCCCCCACCACCCGCGGCTGCCGCGGC
GTCCGCTGCGCCGCCGACATCGTCGGCCAGTGCCCCGCC-3'

FIG. 3E (64 NUCLEOTIDES).
5'-AGACGGTGCAGGCGTCGTTGCAGCCGCCGCCGGGGGCCTTGAGCT
TGGCGGGGCACTGGCCGAC-3'

FIG. 3F (101 NUCLEOTIDES).
5'-TCCAGACCTCCGAGTACTGCTGCACCACCGGCAAGTGCGGCCCCA
CCGAGTACTCCCGCTTCTTCAAGCGCCTCTGCCCCGACGCCTTCTCCT
ACGTCCTC-3'

FIG. 3G (107 NUCLEOTIDES).
5'-GCTTGCCTGCAGTTATTATTAGGCGGTGGGGCAGAAGGTGACGCGG
TAGTTGGAGGAGCCGGGGCAGGTGACGGTGGTGGGCTTGTCGAGGAC
GTAGGAGAAGGCGT-3'

FIG. 3H

PREPARATION OF THAUMATIN SWEETENERS

BACKGROUND OF THE INVENTION

1. Technical Field

The present invention relates to genetic engineering and recombinant DNA technology. More specifically, the present invention provides a process for obtaining natural proteinaceous sweeteners of the thaumatin type, new DNA sequences which have been optimized for expression in filamentous fungi and which code for these proteins, and to the use of these sequences in the transformation of filamentous fungi for the production of thaumatin sweeteners.

2. Background Art

The thaumatins are proteins with a very sweet taste and the capacity to increase the palatability (upgrading or improving other flavors) of food. In industry they are currently extracted from the arils of the fruit of the plant *Thaumatoccocus daniellii* Benth. Thaumatins can be isolated from these arils in at least five different forms (I, II, III, b and c), which can be separated using ion-exchange chromatography. These forms are all single-chain polypeptides with 207 amino acids and a molecular weight of approximately 22,000 Daltons. Thaumatins I and II, which predominate in the arils and have very similar sequences of amino acids, are much sweeter than saccharose (100,000 times sweeter according to one estimate). Besides being natural products, thaumatins I and II are non-toxic, making them a good substitute for common sweeteners in the animal and human food industries.

Despite its advantages, industrial use of thaumatins of natural plant origin is very limited because of the extreme difficulty involved in obtaining the fruit from which they are extracted. The producing plant, *T. daniellii*, not only requires a tropical climate and pollination by insects, but it must also be cultivated among other trees and yet 75% of its flowers do not bear fruit.

Attempts have been made to produce thaumatins by genetic engineering in bacteria such as *Escherichia coli* (see published European patent applications EP 54,330, EP 54,331 and WO 89/06283), *Bacillus subtilis* and *Streptomyces lividans*, in yeasts such as *Saccharomyces cerevisiae* (see WO 87/03007) and *Kluveromyces lactis* (EP 96,430 and EP 96,910), in the fungus *Aspergillus oryzae* (Hahm and Batt, *Agric. Biol. Chem.* 1990, vol. 54, pp. 2513–20), and in transgenic plants such as *Solanum tuberosum*. Until now, the results of such production efforts have been considered disheartening. Thus, the thaumatin available to industry is very scarce and expensive (cf. M. Witty and W. J. Harvey, "Sensory evaluation of transgenic *Solanum tuberosum* producing r-thaumatin III", *New Zealand Journal of Crop and Horticultural Science*, 1990, vol. 18, pp. 77–80, and the articles cited therein).

Accordingly, there has remained a need for economically obtaining industrial amounts of thaumatins.

SUMMARY OF THE INVENTION

The present invention overcomes the need for economically obtaining industrial amounts of thaumatins by providing recombinant DNA useful for the expression of large amounts of thaumatins in filamentous fungi.

In one aspect, the present invention provides optimized artificial genes encoding thaumatin proteinatious sweeteners. Preferably, the artificial genes are optimized for use in the transformation of filamentous fungi.

In another aspect, the invention provides recombinant DNA expression vectors (e.g. plasmids) containing an optimized thaumatin gene. The optimized gene is operatively linked to an expression cassette containing a promoter and a termination sequence operable in filamentous fungi, a selectable marker sequence and, optionally, a secretion signal DNA sequence for providing for the extracellular secretion of the expressed thaumatin protein.

The present invention further provides methods for the production of thaumatins by transforming filamentous fungi with the inventive DNA sequences, and to such transformed fungi per se.

The expression of thaumatin fusion proteins also is a part of the present invention.

BRIEF DESCRIPTIONS OF THE DRAWINGS

FIG. 1: (A) DNA sequence showing nucleotides 272–304 SEQ ID NO:5 from the MCS of commercial plasmid pTZ18R. (B) Fragment of plasmid pTZ18RN, obtained from the former, showing its unique NcoI restriction site SEQ ID NO:19.

FIG. 2: Strategy used to build the synthetic gene, with A, B and C representing restriction enzymes for cloning of the oligonucleotide pairs, once they are paired and elongated, on the pTZ18RN vector.

FIGS. 3A–H Sequences of the oligonucleotides used to build the gene, respectively.

FIG. 4: Diagram of the different stages in the construction of the artificial and synthetic gene (sequence represented in black).

FIG. 5: Representative autoradiographs of the gene sequence using the Sanger dideoxy method: (A) the first 60 nucleotides; (B) nucleotides 70–170; (C) nucleotides 330–370.

FIG. 6: Diagram of the manipulations performed to obtain the pThII plasmid.

FIG. 7: Results of the PCR analysis of the two transformed fungi, M0901 and T0901, compared with the pThII plasmid and an untransformed control fungus. On the y-axis, the number of bases according to two standard reference markers is provided.

FIG. 8: Results of the immunoblotting analysis of the transformed fungi from FIG. 7, compared with commercial thaumatin II and an untransformed control fungus (E=extracellular protein; I=intracellular protein). The numbers on the y-axis correspond to protein markers of known molecular weight. The arrow indicates the place where the commercial thaumatin (4) and the recombinant thaumatin migrate (2, 3, 5 and 6).

FIG. 9: Diagram of the manipulations performed to obtain the pThIII plasmid. The sequence corresponding to the sulfanilamide resistance gene ($Su^R$) is shown as the dark crosshatched section and the sequence of thaumatin is shown as the lighter crosshatched section. The section with vertical lines shows the different fungal promoter and terminating sequences, as well as the "signal" sequence of 24 amino acids from the glucoamylase gene (labelled $SSGlaA_{24}$).

FIG. 10: Results of PCR analysis of the A2 transformed fungus (thaumatin secretor). On the x-axis, the number of bases according to standard reference markers. Lanes 1 and 5 correspond to markers, lane 2 contains DNA from an untransformed fungus (control), and lane 3 contains DNA from fungus a2. Lane 4 is a positive control (DNA from the pThIII plasmid).

FIG. 11: Results of the immunoblotting analysis of the transformed fungi T0901 and a2. Lane 1 contains commercial thaumatin. Lane 7 corresponds to protein markers of known molecular weight (the molecular weights of each protein are indicated next to each lane). Lane 2 contains the culture medium in which the T09011 fungus was grown, a producer of intracellular thaumatin. Lanes 3 and 4 contain the culture medium in which the a2 fungus was grown (extracellular producer) and an untransformed fungus (control). Lanes 5 and 6 contain mycelium from these two fungi, respectively.

FIG. 12: Diagram of the manipulations performed to obtain the pECThII plasmid. The dark crosshatched section represents the synthetic gene of thaumatin II.

FIGS. 13A and 13B: Diagram of the manipulations performed to obtain the pThIX plasmid. The dark crosshatched section is the glucoamylase (glaA) sequence of *Aspergillus niger* or *Aspergillus niger* var. *awamori*. The wavy line section represents the glutathione-S-transferase sequence of *Escherichia coli*. The synthetic gene codifying thaumatin II appears as the lighter grey crosshatched section and the spacer sequence is between the genes of thaumatin and glucoamylase with vertical lines.

FIG. 14: Details of the sequences in the fusion area between glucoamylase and thaumatin.

DETAILED DESCRIPTION OF THE PREFERRED EMBODIMENTS

Figure 2:
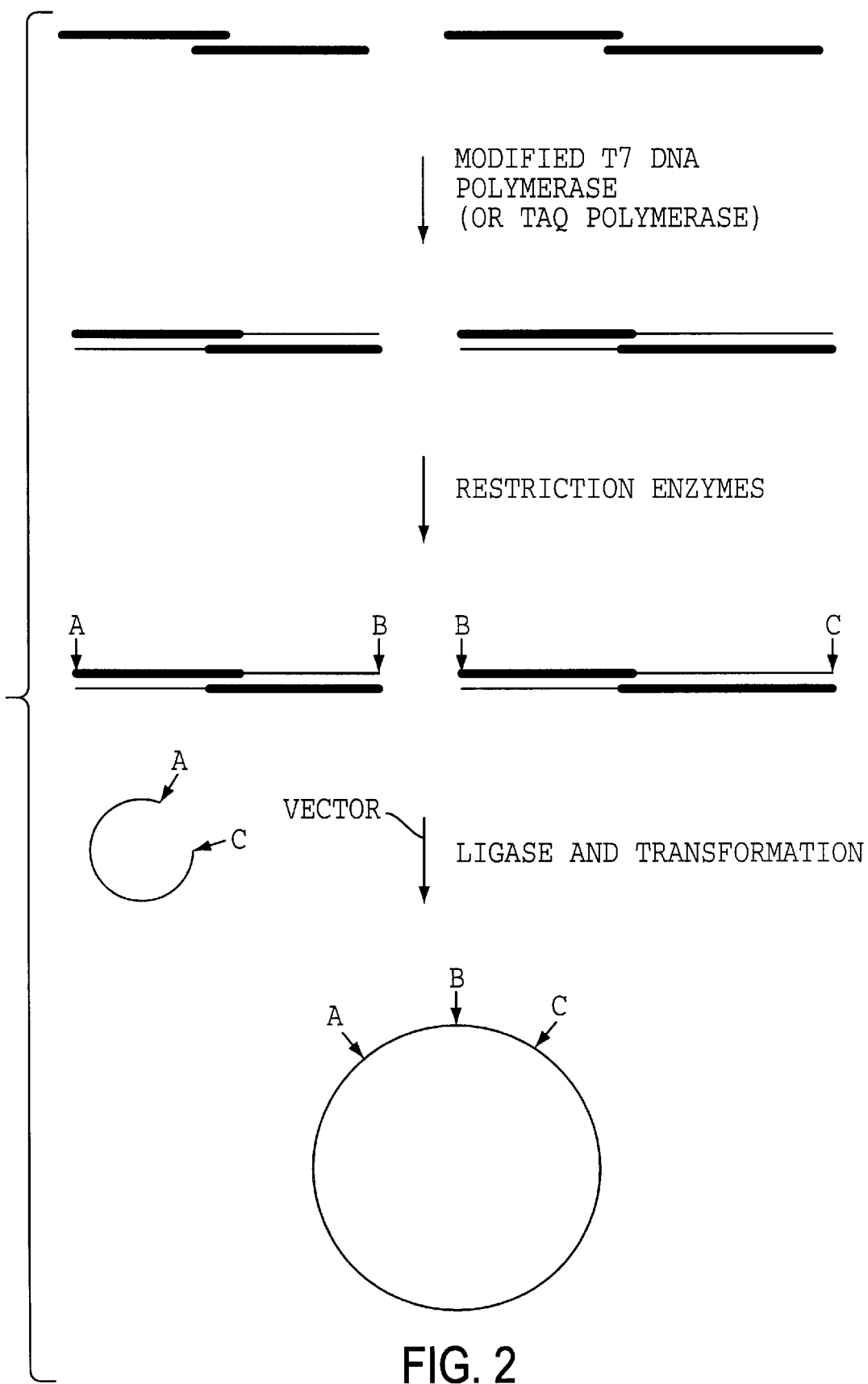

This invention is directed to the preparation of thaumatins, especially thaumatins I and II, through their expression in filamentous fungi without using natural DNA (or derived cDNA) as has previously been described for the fungus *Aspergillus oryzae*. Rather, artificial, synthetic and substantially optimized genes are used for expression in filamentous fungi. The genes are optimized according to specific rules, disclosed herein, for substituting amino acid codons for those naturally occurring in the thaumatin gene. Obtaining substantially optimized artificial genes for filamentous fungi allows for high expressions of protein, making the process useful and economically viable for industrial (commercial) applications.

In a specific embodiment of this invention, the filamentous fungi used for protein expression are considered innocuous, and those included on the GRAS list (Generally Recognized as Safe) are especially preferred. Preferred GRAS fungi include the Penicillium genus, especially the species *Penicillium roquefortii*, and the Aspergillus genus, especially the *niger* species and the *niger* variant *awamori*.

This invention encompasses obtaining thaumatins I and II secreted extracellularly (for which an appropriate secretion signal is introduced in the plasmid), and obtaining thaumatins I and II intracellularly, which allows for their use in animal food, without prior separation of the mycelium from the fungi.

The following abbreviations are used below, among others:
A=Adenine
Amp=Ampicillin
ATP=Adenosine triphosphate
BSA=Bovine serum albumin
C=Cytosine
CIP=Calf intestinal phosphatase
dATP=2'-Deoxyadenosine triphosphate
dCTP=2'-Deoxycytidine triphosphate
dGTP=2'-Deoxyguanosine triphosphate
DNA=deoxyribonucleic acid
DTT=1,4-Dithiothreitol
dTTP=2'-Deoxythymidine triphosphate
EDTA=Ethylenediaminetetra-acetic acid (disodium salt)
G=Guanine
GRAS=Generally regarded as safe
KDa=Kilodalton
MCS=Multiple cloning site
nt=Nucleotides
bp=base pairs
PCR=Polymerase chain reaction
PEG=Polyethylene glycol
PMSF=Phenylmethylsulfonyl fluoride
rpm=revolutions per minute
SDS=Sodium dodecyl sulphate
SSC=Sodium sodium citrate (0.15M NaCl; 0.015M sodium citrate)
T=Thymine
TE=Buffer 10 mM Tris-HCl, pH 8.0; 1 mM EDTA
U=Units
X-gal=5-bromo-4-chloro-3-indo-β-D-galactose
Amino acids are designated by their standard abbreviations. For plasmids, the published notation in each case is used.

In one aspect, this invention provides a new gene for codifying thaumatin II which is artificial, synthetic and more than 50% optimized for expression in filamentous fungi. This gene consists of a DNA sequence which codifies the sequence of amino acids of Sequence ID No. 2 (corresponding to the 207 amino acids of the protein thaumatin II). This DNA sequence is the result of making more than 50% of the possible modifications of the DNA sequence of the natural gene which codifies the 207 amino acids of thaumatin II (which gene is described in the literature and also included in Sequence ID No. 1) through (A) the addition of one or more (n in Sequence ID No. 1) stop codons selected from TAA, TAG, TGA and (B) performing more than 50% of the possible changes to the nucleotide codons corresponding to the thaumatin II amino acids. The nucleotide sequence changes are made by substituting the codon in parentheses in the following list of amino acid codons for the original codon present in the naturally-occurring gene:

| Ala | (GCC), | Arg | (CGC), | Asn | (AAC), | Asp | (GAC), | Cys | (TGC), |
|---|---|---|---|---|---|---|---|---|---|
| Lys | (AAG), | Gln | (CAG), | Glu | (GAG), | Gly | (GGC), | Ile | (ATC), |
| Leu | (CTC), | Met | (ATG), | Phe | (TTC), | Pro | (CCC), | Ser | (TCC), |
| Thr | (ACC), | Trp | (TGG), | Tyr | (TAC), | Val | (GTC). | | |

The invention also relates to the optimized gene followed by n stop sequences, where integer n is greater than or equal to 1.

As stated above, at least about 50% of the thaumatin gene is optimized for expression in filamentous fungi. Preferably, more than 75% of the gene is optimized (meaning that more than 75% of the codons are selected from the above list). It is even more preferred when the optimization is maximum (100%), i.e., when the DNA sequence of the artificial gene is obtained from the Sequence ID No. 1 sequence by performing 100% of all of the possible codon changes. The fully-optimized thaumatin II gene is seen in Sequence ID No. 3. Also preferred are the previous genes where n is between 1 and 3.

Another part of the subject-matter of this invention is a thaumatin I gene which is artificial, synthetic and more than 50% optimized for its expression in filamentous fungi. This gene consists of a DNA sequence which codifies the sequence of amino acids corresponding to the 207 amino acids of the protein thaumatin I (sequence of 207 amino acids which differs from those of Sequence ID No. 2 in only five amino acids, i.e., 46-Asn, 63-Ser, 67-Lys, 76-Arg and 113-Asn). This optimized DNA sequence is obtained by leaving the following five codons unchanged: AAC (46-Asn), TCC (63-Ser), AAG (67-Lys), CGC (76-Arg) and AAC (113-Asn). The remainder of the codons are modified (optimized) as described above in connection with the thaumatin II gene. One or more stop codons are also added to the gene, as described above. The gene which codifies thaumatin I and which is more than 75% optimized is particularly preferred. It is even more preferred when the optimization is maximum (100%). Artificial genes to which between one and three stop codons have been added are preferred.

Hereinafter, any gene optimized more than 50%, more than 75% or up to 100% is called without distinction a "substantially optimized gene."

This invention also relates to recombinant expression vectors (e.g. plasmids) made up of: (i) a substantially optimized gene coding for thaumatin I or II, operatively linked to an expression cassette for filamentous fungi containing an appropriate promoter sequence and a terminating sequence for this type of fungi, (ii) an appropriate selection marker, and (iii) an optional secretion signal DNA sequence for causing the extracellular secretion of the expressed protein.

Particularly preferred are recombinant plasmids in which the promoter sequence of the expression cassette comes from the glyceraldehyde 3-phosphate dehydrogenase gene of *Aspergillus nidulans*, the terminating sequence of the expression cassette is the tryptophan C sequence of *Aspergillus nidulans* and the selection marker is sulfanilamide resistance. Also preferred are the recombinant analogue plasmids where the promoter sequence of the expression cassette comes from the glucoamylase gene of *Aspergillus niger*.

In a particular embodiment of this invention, the recombinant plasmids express a thaumatin-glucoamylase fusion protein. These plasmids comprise (i) an appropriate selection marker; (ii) a DNA sequence made up of (a) a substantially optimized gene for the expression of thaumatin I or II, (b) a spacer sequence which in turn contains a KEX2 processing sequence, and (c) the complete glucoamylase gene (glaA) of *Aspergillus niger* or *Aspergillus niger* var. *awamori;* and (iii) the "pre" and "pro" signal sequences of the glaA gene.

Part of the subject-matter of this invention are the cultures of filamentous fungi capable of producing the proteins thaumatin I or II, which have been transformed with any of the above-mentioned plasmids. In particular, the filamentous fungi of the species *Penicillium roquefortii, Aspergillus niger* and *Aspergillus niger* var. *awamori* are preferred.

The subject-matter of this invention also includes production processes for thaumatin I or II which include the following steps:

a) incorporation of a substantially optimized gene for the expression of thaumatin I or II, in an expression vector selected from those corresponding to the above-mentioned plasmids using standard recombinant DNA technology techniques;

b) transformation of a strain of filamentous fungus with the previous expression vector;

c) culture of a filamentous fungus strain transformed in this way in the appropriate nutrient conditions to produce thaumatin I or II, either intracellularly, extracellularly or through both methods simultaneously, or in the form of the fusion protein thaumatin-glucoamylase; and d) depending on the case, separation and purification of thaumatin I or II alone, or separation of thaumatin I or II from the culture medium, together with the fungal mycelium.

In a preferred process, the filamentous fungus is selected from the species *Penicillium roquefortii, Aspergillus niger* or *Aspergillus niger* var. *awamori*.

Figure 6:
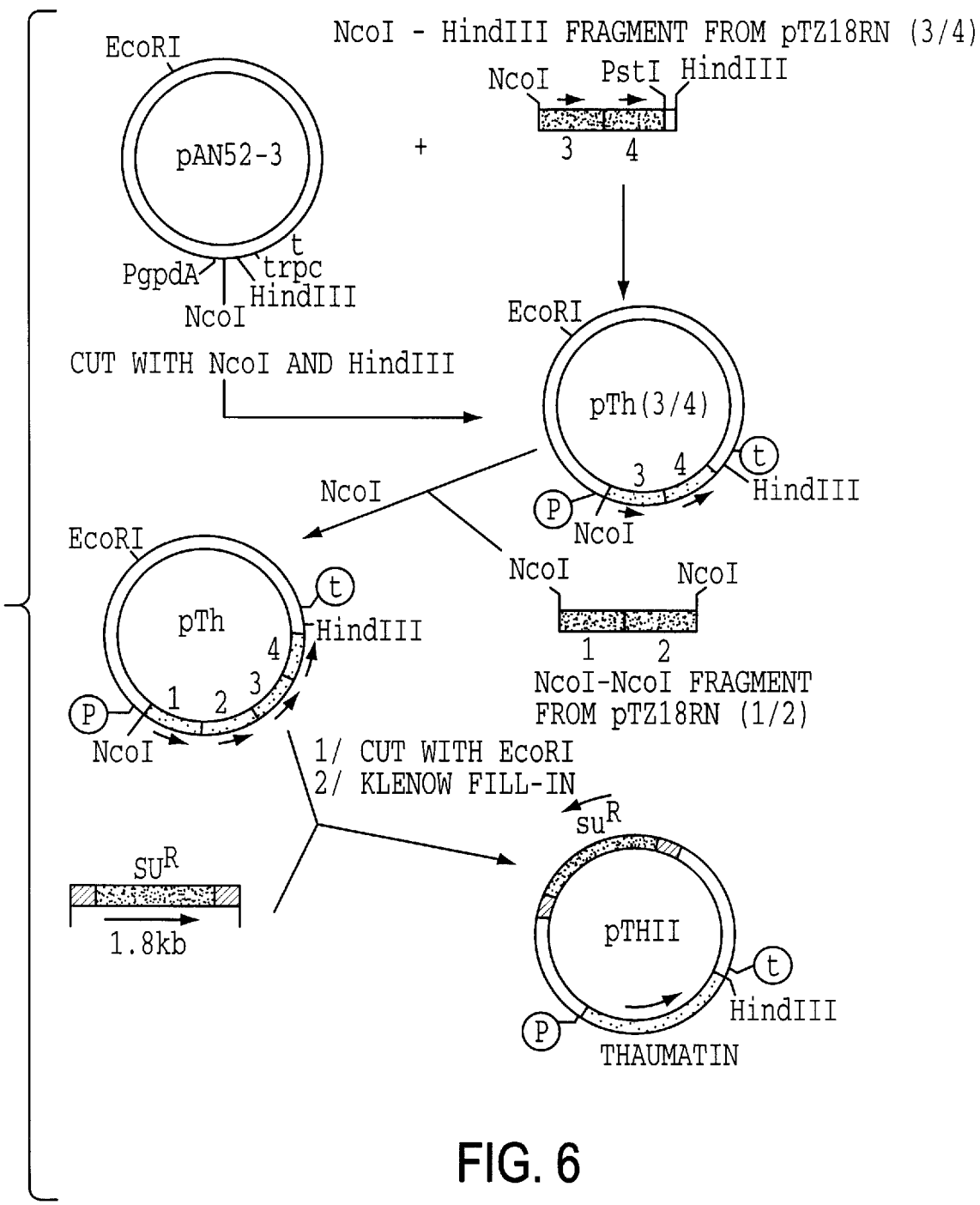

To obtain thaumatin II, pThII recombinant plasmids are preferred, which can be obtained through the method described in the examples and illustrated in FIG. 6, which can be summarized as follows: a) starting with plasmid pTZ18RN(¾), a fragment (¾) of the DNA sequence of the substantially optimized gene which codifies thaumatin II is obtained; b) this fragment is ligated with plasmid pAN52-3, generating plasmid pTh(¾); c) starting with plasmid pTZ18RN(½), the remaining fragment (½) of the DNA sequence of the substantially optimized gene which codifies thaumatin II is obtained; d) this fragment is ligated to plasmid pTh(¾), generating plasmid pTh; e) a DNA fragment is inserted to provide resistance to sulfanilamide, Su$^r$, thus obtaining plasmid pThII (FIG. 6). With this plasmid, thaumatin II is obtained primarily intracellulary.

For the extracellular production of thaumatin II in *Penicillium roquefortii*, pThIII plasmids are preferred. The preparation of pThIII is described in Example 2 and is outlined in FIG. 9. To prepare it in *Aspergillus niger* var. *awamori*, the process described in Example 3 is used.

Thaumatin II is produced as a fusion protein with glucoamylase through the use of the pECThII and pThIX plasmids. The preparation of these plasmids is described in the examples and outlined in FIGS. 12, 13A and 13B.

To produce thaumatin I, the recombinant plasmids obtained following methods analogous to those used to produce thaumatin II are used. Thus, for example, for intracellular production in *Penicillium roquefortii*, pThI plasmids are used which are obtained as follows: a) Starting with plasmid pTZ18RN(½), the fragment (½) of the substantially optimized gene sequence is obtained which codifies thaumatin II; b) this fragment is ligated to plasmid pTZ18RN(¾) linearized with NcoI, thus generating plasmid PTZ18RN(Th); c) starting with plasmid pTZ18RN(Th) in single-stranded form and using site-directed mutagenesis techniques, the following changes are carried out on the sequence of the synthetic and artificial gene of thaumatin II, where the symbol → joins the replaced (original) and the replacement (final) in this order:

AAG → AAC (46-Lys → 46-Asn)
CGC → TCC (63-Arg → 63-Ser)
CGC → AAG (67-Arg → 67-Lys)
CAG → CGC (76-Gln → 76-Arg)
GAC → AAC (113-Asp → 113-Asn)

this plasmid is then called pTZ18RN(ThI); d) starting with plasmid PTZ18RN(ThI) a DNA fragment of the complete sequence of the substantially optimized gene which codifies thaumatin I is obtained; e) this fragment is ligated to plasmid pAN52-3, thus generating plasmid pTh'; f) a DNA fragment containing resistance to sulfanilamide, Su$^R$, is inserted, thus obtaining plasmid pThI.

In a specific embodiment of this invention, the plasmids are replicated and amplified in *Escherichia coli*.

When the filamentous fungus is of the GRAS type, the processes for isolating thaumatin I or II together with the fungal mycelium are particularly interesting. In these cases, a part of the subject-matter of this invention is also the use of mixtures of thaumatin I or II and fungal mycelium obtained in this way to increase the sweetness or palatability of animal food.

When it is necessary to obtain purified thaumatin I or II, the expression vector can be a plasmid which also contains a secretion signal sequence in the DNA so that the filamentous fungus produces thaumatin I or II extracellularly. In some cases the production of thaumatin I or II can be increased by obtaining the fusion protein with glucoamylase.

In specific embodiments of this invention, when obtaining the pThI and pThII plasmids, the promoter sequence of the expression cassette can come from any gene from the following enzymes of filamentous fungi: glyceraldehyde 3-phosphate dehydrogenase, β-glucoamylase, alcohol dehydrogenase, glucoamylase or α-amylase. Moreover, the terminating sequence of the expression cassette can be the sequence corresponding to the promoter sequence in question. Selection markers that confer resistance to sulfanilamide, oleomycin, hygromycin B, phleomycin or acetamide can be employed.

As shown in the examples, this invention makes it possible to obtain thaumatin I or II for commercial uses with satisfactory phenotypical characteristics, and with high productivity, which represents a considerable advantage over the state of the art. Moreover, because the fungus is harmless, the thaumatin can be administered together with the mycelium, a fact which saves time in the purification process and, therefore, represents a considerable additional advantage, especially for use in animal food.

Without being limiting, the following detailed examples illustrate this invention. The culture of the fungus *Penicillium roquefortii*, which produces the thaumatin II obtained in Example 1, has been deposited in the Spanish Collection of Standard Cultures (Colección Española de Cultivos Tipo, CECT) of the Departmento de Microbiología of the Facultad de Ciencias Biológicas of the University of Valencia, as deposit number CECT 2972.

EXAMPLES

Example 1

Intracellular Production of Thaumatin II in Penicillium Roquefortii (1.1) Construction of the Synthetic, Artificial and Completely Optimized Gene Encoding Thaumatin II (1.1.1) Optimization of the DNA sequence of thaumatin II Starting with the known amino acid and nucleotide sequences of thaumatin II and its corresponding natural gene (see for example EP 54,330), reproduced in Sequence ID No. 1 and Sequence ID No. 2, the sequence of optimized DNA of Sequence ID No. 3 was designed, which codifies the same protein and where n=3 (3 TAA stop codons). The optimized sequence of Sequence ID No. 3 was obtained by performing the maximum number of changes on the codons of Sequence ID No. 1, replacing the original codons with the codons indicated in parenthesis on the following list of amino acid codons, when the latter were different from the originals:

| | | | | | | | | | |
|---|---|---|---|---|---|---|---|---|---|
| Ala | (GCC), | Arg | (CGC), | Asn | (AAC), | Asp | (GAC), | Cys | (TGC), |
| Lys | (AAG), | Gln | (CAG), | Glu | (GAG), | Gly | (GGC), | Ile | (ATC), |
| Leu | (CTC), | Met | (ATG), | Phe | (TTC), | Pro | (CCC), | Ser | (TCC), |
| Thr | (ACC), | Trp | (TGG), | Tyr | (TAC), | Val | (GTC). | | |

(1.1.2) Construction of the pTZ18RN recombinant plasmid using site-directed mutagenesis Before beginning assembly of the synthetic gene for thaumatin II, a single restriction site for NcoI was inserted in the multiple cloning site (MCS) of the multifunctional plasmid pTZ18R (supplied by Pharmacia Inc.). In this way plasmid pTZ18RN was generated ("IN" denotes the presence of the NcoI restriction site), the restriction site of which is shown in FIG. 1. The insertion of the restriction site for NcoI was performed using the site-directed mutagenesis technique described below:

Oligonucleotide p115 (5'-ACCCGGGGATCCT CTCCATGGGACCTGCAGGCATGCA-3') SEQ. ID NO:14 was supplied by Ingenasa S. A. (Madrid, Spain). Using standard procedures (Maniatis et al., "Molecular Cloning, A Laboratory Manual", Cold Spring Harbor Laboratory Press, 1989), this oligonucleotide was labeled at the 5' end by transferring $^{32}$P from [gamma-$^{32}$P]ATP with polynucleotide kinase. pTZ18R, with its DNA in single-stranded form, was obtained by standard techniques and was hybridized with one picomol of oligonucleotide labelled with $^{32}$P at its 5' end in a buffer containing 40 mM Tris.HCl, pH 7.5, 50 mM NaCl and 20 mM MgCl$_2$ (final volume 5 μL). The mixture was incubated at 65° C. for five minutes and allowed to cool slowly (overnight) to room temperature. The following enzymes and reagents were then added to the 5 μL of this mixture: 1.5 μL of B 10× solution (200 mM Tris.HCl, pH 7.5; 100 mM MgCl$_2$; 50 mM DTT) ; 1 μL of 10 mM ATP; 4 μL of a mixture containing 2.5 mM of each of the 4 dNTPs (dATP, dGTP, dTTP, dCTP); 6.5 μL of water; 1 μL of T4 DNA polymerase (3 units/μL); and 1 μL of DNA ligase (6 units/μL). The reaction mixtures were incubated for 3 hours at room temperature and at the end of that time 1 μL of T4 DNA polymerase was added (3 units) and 1 μL of DNA ligase (6 units). The reactions were continued for 60 more minutes at 37° C.

Aliquots of 1.0 μL of each reaction mix were used to transform *E. coli* strain JM103. Various colonies grown in LB/ampicillin (100 μg/mL) dishes were replated in dishes with fresh medium (LB=Luria broth, a culture medium with the following composition: 1% bacto-tryptone, 0.05% yeast extract, 170 mM NaCl, pH 7.0) and analyzed. To be able to identify the clones containing the desired mutation, the colonies were analyzed using the p115 oligonucleotide labelled with [gamma-$^{32}$P]ATP as a probe, as described below.

Candidate colonies were replated in nitrocellulose filters (Schleicher & Schuell). The filters were placed in LB/amp dishes and incubated overnight at 37° C. The next day the cells were lysed by successively washing the filters in three solutions:

—Five minutes in 0.5M Tris.HCl, pH 7.5, 1M NaCl.
—Five minutes in 1M Tris.HCl, pH 7.5.
—Five minutes in 0.5M Tris.HCl, pH 7.5, 1M NaCl.
The filters were then dried at 80° C. for 90 minutes. Once they were dry the filters were washed three times in 3× SSC, 0.1% SDS. Pre-hybridization took place in a solution containing 6× SSC, 5× Denhardt solution, 0.05% sodium pyrophosphate, 100 µg/ml of boiled salmon sperm DNA, and 0.5% SDS. Filters were pre-hybridized for one hour at 37° C. Hybridization took place overnight in 50 mL of the same solution, to which 33 ng of labelled p115 probe was added. The hybridization temperature was 50° C. On the next day the filters were washed as follows:
—First wash: 15 minutes in 2× SSC, 0.1% SDS, at room temperature.
—Second wash: the same conditions, but at 55° C.
—Third wash: The same conditions, but at 65° C.
—Fourth wash: 15 minutes in 0.4× SSC, 0.1% SDS at 65° C.
After the fourth wash, the filters were exposed to an X-ray film for 2 hours at −20° C. Various colonies with DNA showing marked hybridization to probe 115 were identified and DNA was extracted from each.

The final identity of the clones was verified by testing if the DNA could be cut or not cut with NcoI and by analyzing its sequence. The plasmid containing the NcoI restriction site between BamHI and PstI (FIG. 1) was called pTZ18RN and was the parent vector used in the construction of the artificial, synthetic and totally optimized gene for thaumatin II.

(1.1.3) Strategy for building the synthetic gene which codifies thaumatin II

The method for assembling the synthetic gene of thaumatin II is shown in FIG. 2. The eight long oligonucleotides whose sequences are shown in FIGS. 3A–H were supplied by Isogen Bioscience, Inc. (Netherlands). The single-stranded oligonucleotides, which occur in pairs, can be paired because of the complementary nature of the sequences. They were labelled 1a, 1b,; 2a, 2b; 3a, 3b; and 4a, 4b. After pairing, the single-stranded areas were filled with modified T7 DNA polymerase (Taq DNA polymerase can also be used). The resulting double-chain fragments were digested with the appropriate restriction enzymes to obtain cohesive ends or blunt ends and then ligated to the desired vector.

Figure 4:
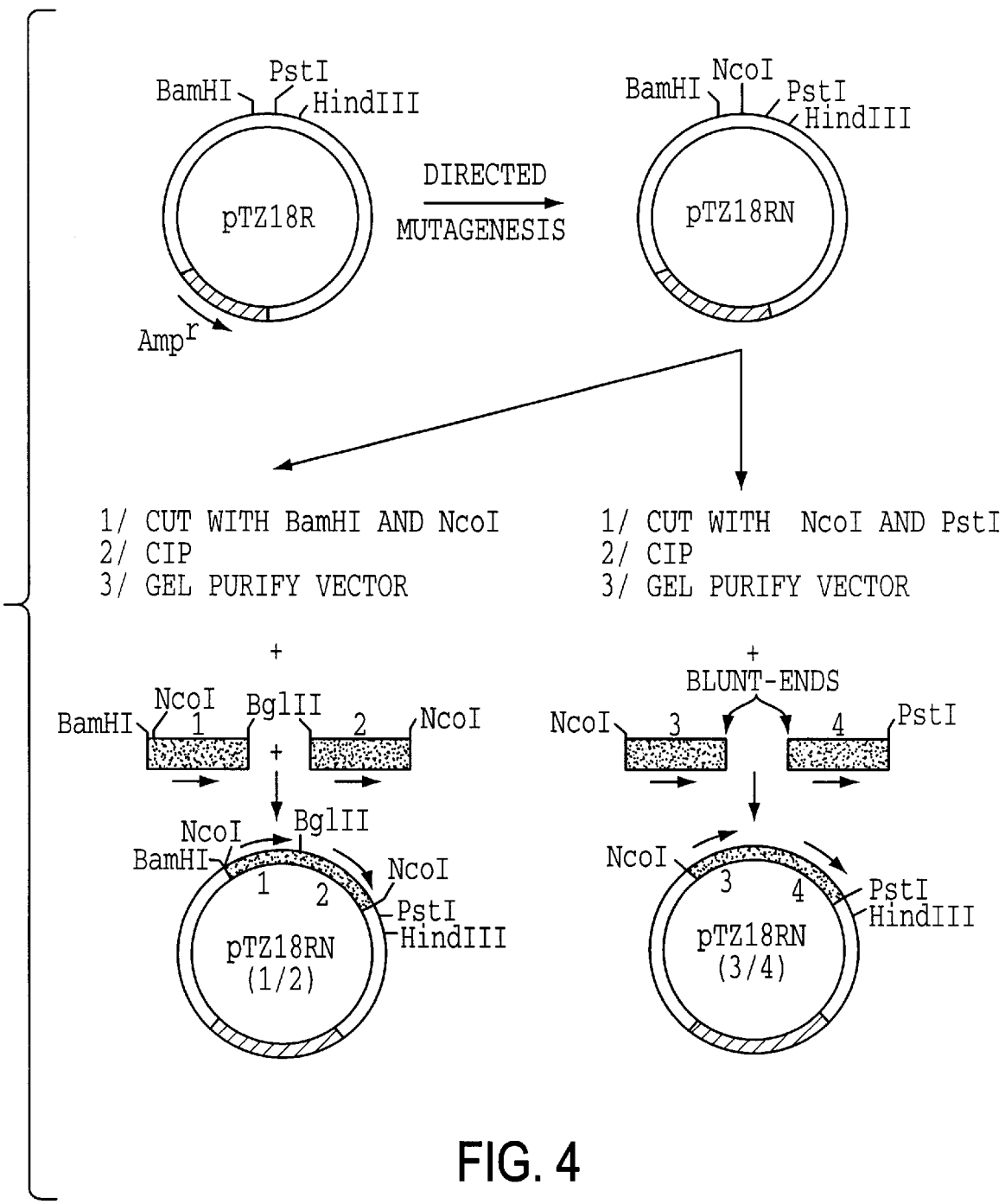

FIG. 4 shows the strategy used to build the synthetic gene in 2 fragments, which were then joined to an expression vector.

(1.1.3.1) Assembly of the first 332 pairs of bases of the synthetic gene of ID Sequence No. 3 (n=3).

In the first stage, the oligonucleotides 1a, 1b, 2a and 2b were joined to obtain a DNA fragment with 332 base pairs which could be inserted in the pTZ18RN plasmid.

One microgram of oligonucleotide 1a and 1 µg of 1b were mixed in a buffer solution containing 40 mM Tris.HCl, pH 8.0, 10 mM MgCl$_2$, 5 mM DTT, 50 mM NaCl and 50 µg/mL of bovine serum albumin (BSA). The mixture (17 µL) was heated for 5 minutes at 70° C. and then cooled slowly to 65° C. for about ten minutes (appropriate temperature for hybridizing the pairs of oligonucleotides). Then 2 µL of a mixture of the four deoxynucleotides was added (2.5 mM of each dNTP) and 1 µL of the modified T7 DNA polymerase enzyme (Sequenase brand from U.S. Biochemical Corp.), giving a final volume of 20 µL. The reactions took place for 30 minutes at 37° C., followed by 10 additional minutes at 70° C. (to inactivate the Sequenase). The reaction products were digested with Bam HI and Bgl II at 37° C. for 3 hours.

The DNA's were extracted once with phenol, once with phenol:chloroform and once with chloroform, and were then precipitated with ethanol. The DNA's were finally frozen in TE buffer at −20° C. until later use.

The 2a and 2b oligonucleotides were processed in the same way except that the final products were digested with Bgl II and Nco I.

Plasmid pTZ18RN was digested sequentially with Bam HI and Nco I and was dephosphorylated with calf intestinal phosphatase (CIP). The linearized fragment of 2871 bp bases was recovered from 0.8% agarose gel and then purified.

The products of reactions 1 and 2 were then joined with the linearized pTZ18RN and the mixture was used to transform E. coli strain NM522. To identify the clones with the insert, a white/blue indicator test was used which works as follows:

The pTZ18R plasmid and its derivative pTZ18RN contain the bacterial gene LacZ'. Therefore, the bacterial colonies containing this plasmid are blue on dishes with LB/ampicillin which also contain the chromogenic substrate 5-Bromo-4-chloro-3-indo-β-D-galactose (X-gal). When a fragment of foreign DNA is inserted in the multiple cloning site (MCS) of the pTZ18RN plasmid, the LacZ' gene is deactivated and the resulting colonies are not blue, but white. Therefore, the white colonies were initially isolated, given that they were candidates for containing the different fragments of the synthetic gene of thaumatin II.

Various colonies with inserts of the appropriate size contained complete fragments of the 325 base pairs of the synthetic gene of thaumatin II. The resulting plasmid was called pTZ18RN(½).

(1.1.3.2) Assembly of the second 305 bp's of the synthetic gene of ID Sequence No. 3 (n=3)

In this case, an alternative approach was put into practice using Taq DNA polymerase and the PCR technique. Before the annealing stage, oligonucleotides 3b and 4a were labelled at their 5' ends with a phosphate group using standard techniques. The oligonucleotides were called 3b* and 4a*.

One microgram of 3a and 1 µg of 3b* were incubated in a reaction mix (18 µL) containing 10 mM Tris.HCl, pH 8.4, 50 mM KCl, 1.5 mM MgCl$_2$ and 0.1 mg/ml of gelatin. The samples were incubated for 5 minutes at 70° C. and for five more minutes at 65° C. At this point, each dNTP was added (G, A, T, C) at a final concentration of 2 mM and 2.5 units of AmpliTaq DNA polymerase (Perkin-Elmer Cetus). The PCR reactions were performed as follows: 1 minute at 94° C.; 1 minute at 55° C.; and 1 minute at 72° C. for 30 cycles, followed by a final extension at 72° C. for 5 minutes. The samples were then extracted with phenol:chloroform and resuspended in 10 µL of TE buffer and incubated with Nco I at 37° C. for 3 hours. After extracting and precipitating with ethanol, the DNA's were dissolved in TE buffer and frozen at −20° C. until later use.

The 4a* and 4b oligonucleotides were processed as described above, except that the final products were digested with Pst I.

Ligation of the three fragments was done as per the same process mentioned above, except that pTZ18RN was used, which was cut with Nco I and Pst I, treated with calf intestinal phosphatase and finally purified from an agarose gel. The ligation reactions contained 15% polyethylene glycol (PEG), which stimulates ligations with blunt ends. The ligation products are used to transform E. coli NM 522. A white/blue selection was made again of the recombinants on dishes with LB/amp medium supplemented with X-gal and IPTG. After analyzing the transformants, one clone was isolated which contained the 305 bp fragment of the second part of the thaumatin II gene. This plasmid was called pTZ18RN (¾).

(1.1.3.3) Sequence Analysis

Figure 5A:
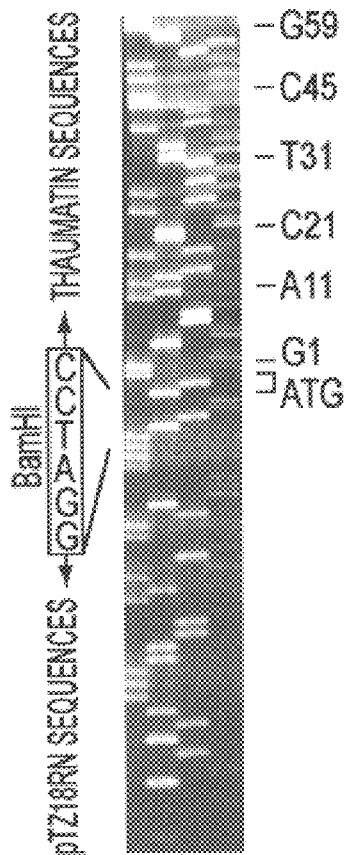
Figure 5B:
Figure 5C:
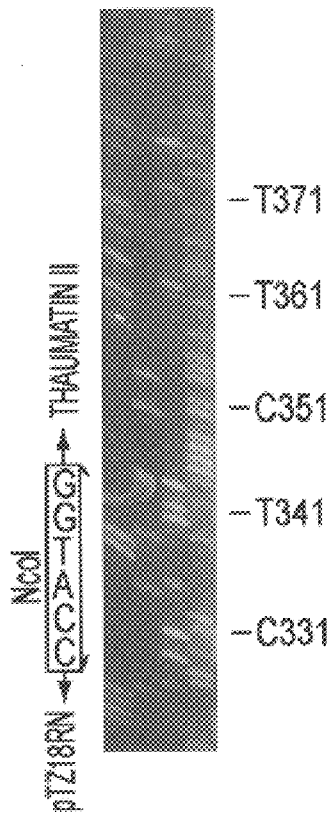

The identity of the synthetic gene was verified by analyzing its sequence using the Sanger method (Sanger, F. et al., Proc. Nat. Acad. Sci. USA 1977, vol. 74, p. 5463–67). A sequencing kit was used (version 2.0) from United States Biochemical Corp. The sequence of the synthetic gene was determined without ambiguity by: (1) sequencing the two gene strands; and (2) performing parallel sequencing reactions with dITP to destabilize the potential secondary structures which could form due to the GC-rich areas. Representative autoradiographs are shown in FIG. 5.

(1.2) Insertion of the Gene in an Expression Vector for Filamentous Fungi (FIG. 6)

In this example, the pAN52-3 plasmid (described in Punt, P. J. et al., *Journal of Biotechnology*, 1990, vol. 17, pp. 19–34; called "starting plasmid" hereinafter) was the starting plasmid for construction of the expression vector in filamentous fungi (pThII) used to transform *Penicillium roquefortii*. Ligating the synthetic gene to this starting plasmid was performed in three stages described below.

(1.2.1) Ligating the ¾ fragment

Thirty micrograms of pTZ18RN(¾) was cut sequentially with Nco I and Hind III, generating 2 fragments. The small fragment with 310 bp containing the second part of the synthetic gene was purified in a 2% agarose gel. At the same time, 5 μg of the starting plasmid was cut sequentially with Nco I and Hind III. It was then dephosphorylated with alkaline phosphatase and a fragment of 5.8 Kb was isolated in 0.8% agarose. Then the starting plasmid, cut with Nco I and Hind III, dephosphorylated and purified, was ligated with the fragment of 310 bp from pTZ18RN(¾). The mixture was used to transform *E. coli* DH5αF' as shown in FIG. 6. The clones containing the desired construction were identified by cutting the recombinant plasmids pTh(¾) with Nco I and Hind III.

(1.2.2) Ligating fragment ½

In a second stage, plasmid pTZ18RN(½) was cut with Nco I and a NcoI-NcoI fragment containing the first part of the gene was purified in a 4% agarose gel. The pTh(¾) plasmid was linearized with Nco I and dephosphorylated with alkaline phosphatase. It was then ligated with the NcoI-NcoI fragment from pTZ18RN(½). The resulting plasmid was called pTh.

To analyze the clones, the pTh plasmid was with Bal I and Hind III. In the clones with the appropriate orientation, a fragment of 625 bp was obtained while those with inappropriate orientation produced a fragment of 300 bp.

(1.2.3) Ligating with the fungal marker

The pTh plasmid was then cut with Eco RI and the 5' ends were filled-in with the Klenow fragment of DNA polymerase I. This treated plasmid was then purified in a 0.8% agarose gel.

Starting with plasmid pEcoliR388 (N Datta, Saint Mary's Hospital, London), the sulfanilamide resistance sequence was obtained, and a construction was made eliminating the procaryote promotor and terminator; the structural gene was then placed under the control of a promotor and a terminator of filamentous fungi (TrpC). The sulfanilamide resistance sequence obtained in this way was cut with SmaI and XbaI; the 5' ends were filled with Klenow and dNTP and a 1.75 Kb fragment was isolated from a 4% agarose gel. Then the fragment obtained in this way was ligated with pTh and transformation was carried out in *E. coli* DH1. The resulting plasmid was called pThII. This plasmid contains: (i) the synthetic gene which codifies thaumatin II under the control of a fungal promotor, and (ii) a sulfanilamide resistance marker. The final identity of the plasmid was verified by sequencing as described in section 1.3.3.

(1.3) Transformation of Penicillium Roquefortii With the Aforementioned Fungal Expression Vector (1.3.1) Protoplast preparation The protoplasts of *Penicillium roquefortii* used in the transformation experiments were prepared according to the following process, starting with the MUCL 29148 strain. Conidia were inoculated in 50 mL of MSDPM liquid medium (medium semi-defined for mycelium production, the composition of which is described below). The culture was incubated for 44 hours at 28° C. in a mechanical stirrer at 270 rpm. The mycelium was recovered by filtration, washed with sterile water and resuspended in a 1.2M KCl solution containing 40 mg of lysin enzyme (Sigma) per gram of mycelium. After 4 hours of incubation at 28° C. at moderate stirring speed, protoplasts were obtained. Cell debris was eliminated by glass wool filtration. The protoplast suspension was washed and centrifuged (2000 rpm, 10 min.) twice with a 1.2M KCl solution (10 mL/g). Finally, the protoplasts were resuspended in 1.2M KCl (1 mL/g). This protoplast suspension ($10^7$–$10^8$ prot/mL) was used for the transformation experiments.

(1.3.2) Transformation

The protoplasts were centrifuged (2000 rpm, 10 min.) and then resuspended ($5 \times 10^8$ protoplasts/mL) in solution I: 1.2M KCl; 50 mM Tris.HCl (pH 8), 50 mM $CaCl_2$ and 20% of solution II (see below). They were incubated for 10 minutes at 28° C. Aliquots of 0.1 mL were mixed with DNA (10 μg) from the expression plasmid, which contained the thaumatin II gene. Immediately afterward, 2 mL of solution II [1.2M KCl; 50 mM Tris.HCl (pH 8), 50 mM $CaCl_2$ and 30% PEG 6000] was added. This mixture was incubated for 5 minutes at room temperature. After recovering the protoplasts by centrifugation (2000 rpm, 10 min.), they were resuspended in 1 mL of 1.2M KCl. Finally, aliquots of the protoplasts treated in this way were replated in petri dishes containing an appropriate medium for regeneration of the cell wall and subsequent selection using sulfanilamide (750 μg/mL). Using this transformation method, various strains that are resistant to sulfanilamide were isolated. These strains were analyzed to verify if the synthetic gene of thaumatin II had been incorporated into its genome.

(1.4) Analysis of the Transformants (1.4.1) PCR analysis

Analysis of the transformants obtained as described above to detect the DNA sequences of the synthetic gene of thaumatin II and resistance to sulfanilamide was performed using standard PCR techniques with appropriate oligonucleotides. Specifically, the T1 and T2 oligonucleotides were used, the sequences of which are included in section (1.4.1.2). T1 is complementary to nucleotides 605 and 624 of the upper strand of the synthetic gene of thaumatin II, while T2 is complementary to nucleotides 21 to 46 of the lower strand. Therefore, with these two oligonucleotides it was possible to amplify a fragment of 604 pairs of bases corresponding to oligonucleotides 21 to 624 of the synthetic gene of thaumatin II.

Figure 7:
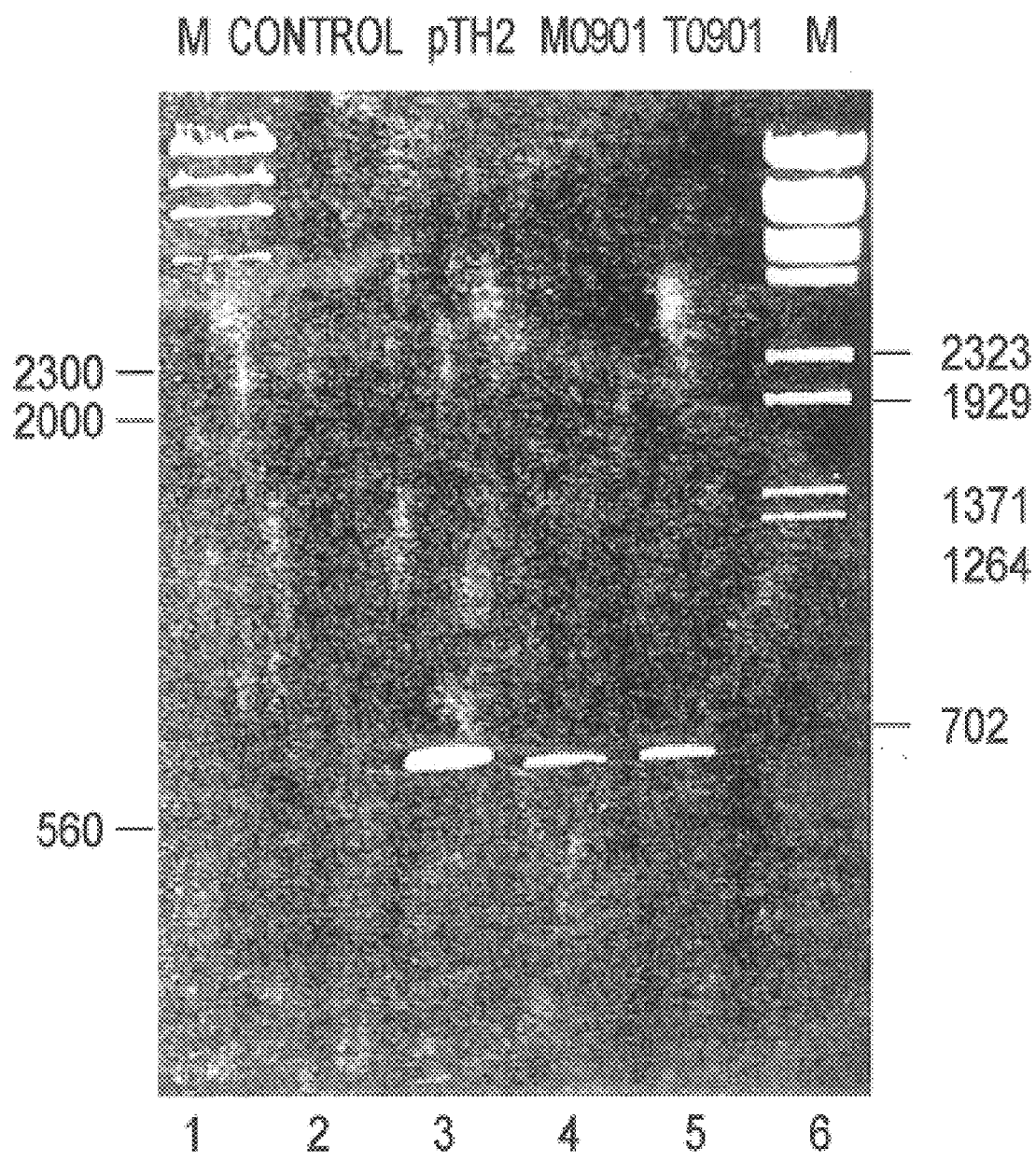

FIG. 7 shows the success of the results, indicating that in the untransformed fungus (control), no bands appear of the size corresponding to the synthetic gene (lane 2), while in two of the transformant genes (M0901 and T0901) bands appear with the same number of bases as the band corresponding to the synthetic gene inserted in the pThII plasmid (lanes 3 to 5).

(1.4.1.1) Extraction of nucleic acids

The starting material was 5 g of mycelium which had been vacuum filtered using a Buchner funnel and which came from a 5-day MSDPM culture (0.6% $NaNo_3$; 0.052% $MgSO_4.7H_2O$; 0.052 KCl; 1% glucose; 0.5% yeast extract; 0.5% casamino acids; $FeSO_4.7H_2O$ traces; $ZnSO_4.7H_2O$ traces).

The mycelium was ground in liquid nitrogen with a porcelain mortar. The mycelium was resuspended in the extraction buffer (10 mM Hepes, pH6.9; 0.3M saccharose; 20 mM EDTA, pH 8.0; 0.5% SDS) at a ratio of 10 mL of buffer per gram of mycelium. It was incubated for 15 minutes at 65° C. and centrifuged for 5 minutes at 7000 rpm (Beckman JA20 rotor) at room temperature to eliminate cell debris; the supernatant was collected and treated twice with phenol/chloroform/isoamyl alcohol (49:49:2) to eliminate proteins. The aqueous phase was precipitated with 0.3M sodium acetate and 2.5 volumes of ethanol for 20 minutes at −20° C. The precipitated volume was centrifuged at 7000 rpm for 20 minutes. The precipitate was resuspended in 1 mL of TE buffer, pH 8.0.

(1.4.1.2) PCR reaction mix

In a total volume of 100 μL, 20 ng of DNA and 10 μL of PEC 10× buffer were mixed (500 mM KCl; 15 mM $MgCl_2$; 100 mM Tris HCl, pH 8.3; 0.01% porcine gelatin; a mixture of DNTPs, with a concentration of 200 μM of each; 2.5 units of Amplitaq and 1 μM of primer). The synthetic oligonucleotides used were T1 (26 nucleotides) and T2 (20 nucleotides) and specific primers for the beginning and end of the synthetic gene of thaumatin II.

T1: 5'-CCGCTGCTCCTACACCGTCTGGGCCG-3' SEQ ID NO:15

T2: 5'-TTAGGCGGTGGGGCAGAAGG-3' SEQ ID NO:16

Twenty μL of mineral oil was added to the mixture to keep the sample from evaporating.

(1.4.1.3) PCR

The sample underwent a cycle at 94° C. for 5 minutes to separate the two DNA strands. Thirty chain reactions were then performed: first the DNA was denatured for 1 minute at 94° C.; the temperature was lowered to 55° C. for 30 seconds to allow the specific primers to join with the denatured DNA strand; the temperature was then increased again to 72° C. for 1 minute to allow the new strand (in formation) to elongate. When all the cycles were completed, a final elongation was performed for 5 minutes at 72° C. The products of each PCR were analyzed in 0.8% agarose gel (FIG. 7). Using this method two strains were identified called M0901 and T0901, the genomes of which contained the synthetic gene of thaumatin II.

(1.4.2) Immunoblotting Detection (Western-Blot)

Figure 8:
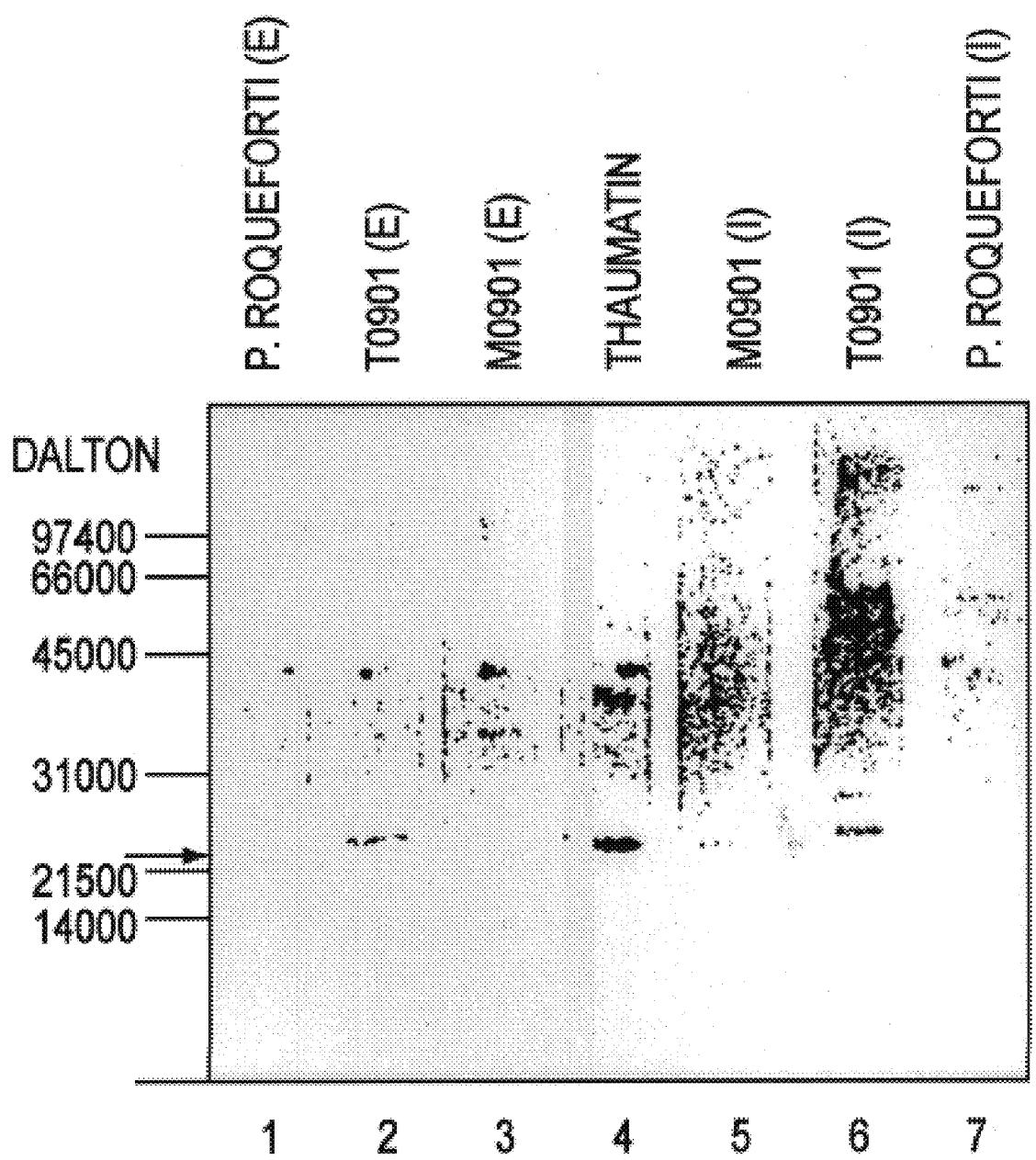

Once the transformants that had incorporated themselves into the thaumatin II gene were detected correctly, Western blot was performed on the expression product (Burnette W. N., *Analytical Biochemistry*, 1981, vol. 112, pp. 195–203), using polyclonal antibodies which had been previously obtained through standard rabbit immunization techniques, to identify the protein. The serum obtained from each rabbit was precipitated with ammonium sulphate using standard techniques to precipitate the immunoglobulins, thus producing a protein fraction enriched with IgG antibodies. FIG. 8 shows the outcome of the results obtained, indicating that no bands of the size corresponding to thaumatin II appear in the untransformed fungus (control), while in two of the transformed fungi a band appears having the same molecular weight as commercial thaumatin II.

(1.4.2.1) Preparation of the samples

The starting material was 2 g of mycelium which had been vacuum filtered using a Büchner funnel and which came from a 5-day culture at 28° C. in MSDPM medium. Both the mycelium retained in the funnel (solid fraction) and in the culture medium (liquid fraction) were analyzed.

Solid Fraction

Ten mL of sonication solution (625 mM Tris.HCl, pH 6.5, 1 mM PMSF, 5% β-mercaptoethanol) per gram of mycelium was added to the mycelium retained in the funnel. The mycelium was sonicated for 1 minute with 1-second pulses (i.e., 1 second sonicated, 1 second without sonication, and so on). The process was repeated three more times at intervals of from 3 to 5 minutes. It was centrifuged at 7500 rpm (Beckman JA20 rotor) for 20 minutes at 4° C.

Liquid Fraction

β-Mercaptoethanol (final concentration 5%) and PMSF (final concentration 1 mM) were added to 3 mL of the extracellular medium. Three mL of both fractions was used to start and was concentrated by column centrifugation (Bio-Rad ultrafilters) which retain the proteins having a molecular weight greater than 10,000 Daltons. In this process, the 3 mL passing through the columns was reduced to 200 μL.

Twenty μL of the 2× sample buffer (25% glycerol; 2.5% SDS; 0.25M Tris.HCl, pH 7.0; 10 mM EDTA, pH 8.0; 0.002% bromophenol blue) was added to 20 μL of the concentrated solutions. They were boiled for 5 minutes and immediately placed in protein denaturing gel (SDS-polyacrylamide).

The protein gels used were 14% polyacrylamide and 18% urea. Electrophoresis was performed at 150 volts and stopped when the front of the sample was 3 or 5 mm from the end of the gel.

(1.4.2.2) Transfer to nitrocellulose

Once the electrophoresis was completed and after removing the piled-up part, the gel was transferred to nitrocellulose paper (NC) using the Bio-Rad Trans-blot SD Semidry Unit. Transfer took 30 minutes at 15 volts.

Once the bands were transferred to NC paper, the paper was left in blocking solution (3% BSA; 0.01% sodium azide; 0.05% Tween-20 in TBS; TBS=150 mM NaCl; 50 mM Tris.HCl, pH 8.0) and stirred overnight. After this operation, the NC paper was processed as follows:

The NC paper was taken out of the blocking solution, washed with TBS and incubated with serum: immune IgG fraction (0.37 mg/mL) diluted (1:500) in blocking solution (with sodium azide). As a negative control, the normal pre-immune IgG fraction was used (0.35 mg/mL) diluted (1:500) in blocking solution (with sodium azide). The solution was stirred and incubated for 4 hours at room temperature.

Three 10-minute washes were performed in TBS-Tween (TBS 1×+Tween-20, 0.05%). It was stirred and incubated for 4 hours at room temperature with the secondary antibody: anti-rabbit IgG-phosphatase alkaline conjugate diluted (1:500) in blocking solution (without sodium azide). Three 10-minute washes were performed in TBS-Tween.

The alkaline phosphatase reaction was performed as follows: a) the NC was equilibrated with alkaline phosphatase buffer (100 mM Tris.HCl, pH 9.5 100; 100 mM NaCl; 50 mM $MgCl_2$); b) the NC was placed in the development reaction mix (15 mL of alkaline phosphatase buffer, 66 μL of nitro blue tetrasodium, NBT) (75 mg/mL in 70% dimethyl formamide), 99 μL of 5-bromo-4-chloro-3-indole phosphate (BCIP) (25 mg/mL in 100% dimethyl formamide) until the bands turned dark; c) the reaction was stopped with alkaline phosphate stop solution (20 mM Tris.HCl, pH 8.0 and 20 mM EDTa, pH 8.0).

(1.4.2.3) Protein gel staining

The gels were stained for 1 hour with staining solution and stirred gently (25 ethanol; 10% acetic acid; 0.1% Coumassie blue). They were destained with destaining solution (25% methanol; 7.5% acetic acid) until the blue color faded from the gel base.

Example 2

Extracellular Production Of Thaumatin In Penicillium Roquefortii

Figure 9:
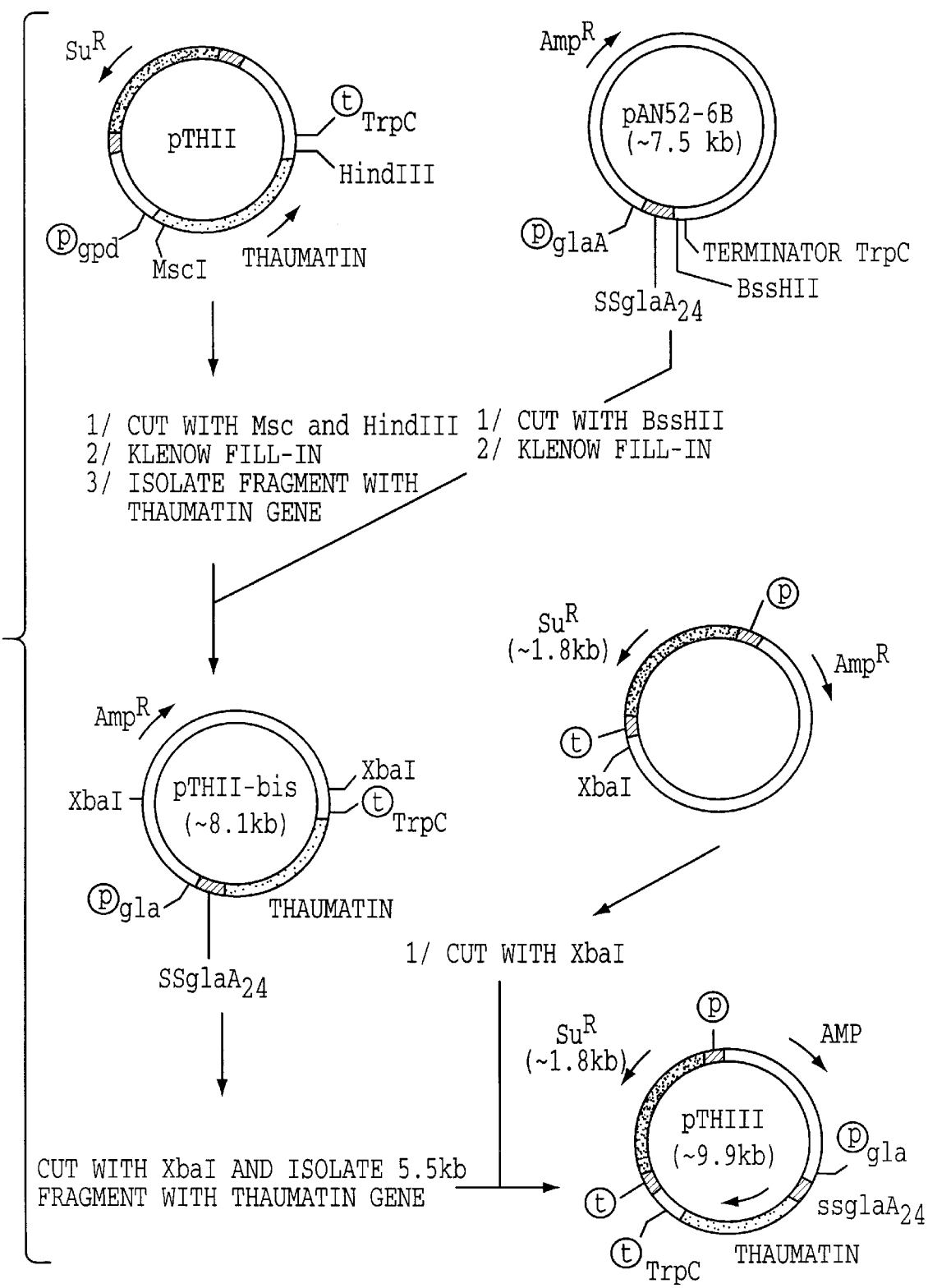

For extracellular production of thaumatin, *Penicillium roquefortii* was transformed with plasmid pThIII, which was constructed as described below and outlined in FIG. 9.

Plasmid pThII described above (section 1.2.3) was purified using standard techniques and resuspended in TE buffer at a final concentration of 1 μg/μl. Thirty micrograms (μg) of this plasmid were cut with restriction enzymes MscI and HindIII, and a fragment of 646 base pairs containing the complete gene of thaumatin II was isolated in a 0.8% agarose gel. The ends of the fragment were converted to blunt ends with the Klenow fragment from DNA polymerase I.

Plasmid pAN52-6B, containing approximately 7.5 Kb and derived from pAN52-6 Not 1 (cf. Van den Hondel et al., "Heterologous Gene Expression in filamentous fungi"; in Bennett and Lasvre, "More Gene Manipulation in Fungi"; Academic Press, 1991, chapter 18, pp. 396–428) was digested with BssHII and its ends were converted to blunt ends through the action of the Klenow fragment of DNA polymerase I. These two fragments were ligated using DNA ligase and the resulting mix was used to transform the DH5αF' strain of *E. coli*. The resulting plasmid, pThII-bis, was isolated and its structure verified by sequencing using the Sanger dideoxy method.

The pThII-bis plasmid (8.1 Kb) was cut with XbaI, and a fragment of approximately 5.5 Kb in length containing the thaumatin gene and the promoter sequence and glucoamylase signal sequence of *Aspergillus niger* was isolated. The trpC terminator sequence of *Aspergillus nidulans* was also present in this fragment.

The aforementioned 5.5 Kb fragment was ligated with a plasmid containing the sulfanilamide resistance sequence, previously cut with XbaI (the only cutting site on this plasmid). The ligating mix was used to transform *E. coli* strain DH5αF'. The resulting plasmid was called pThIII, as indicated in FIG. 9. The pThIII plasmid contained: (i) the synthetic gene which codifies thaumatin II under the control of the glucoamylase promoter of *Aspergillus niger*; (ii) the signal sequence ("pre") and the "pro" sequence of the glucoamylase gene of *Aspergillus niger*; (iii) a sulfanilamide resistance marker; and (iv) the trpC terminator of *Aspergillus nidulans*. The final identity of this construction was verified by sequencing.

A strain of *Penicillium roquefortii* was transformed with plasmid pThIII according to the same method described in Example 1 (sections 1.3.1 and 1.3.2). The colonies resistant to sulfanilamide were tested to see if their genomes contained the substantially modified synthetic gene coding for thaumatin II. The methods used (PCR) were analogous to those described in Example 1 (section 1.4.1).

Figure 10:

FIG. 10 shows the result of a PCR experiment. The two oligonucleotides used to detect the thaumatin gene were the same ones used before (T1 and T2). With these two oligonucleotides, a fragment of 604 pairs of bases can be amplified corresponding to nucleotides 21 to 624 of the synthetic gene encoding thaumatin II. FIG. 10 shows that when DNA from an untransformed fungus ("control", lane 2) is used, none of the bands corresponding to the synthetic gene are amplified, whereas when DNA is used from a fungus transformed with pThIII, a band of the expected size is amplified (lane 3). This fungus was called transformant a2. For control purposes, the reaction products obtained when plasmid pThIII was used were also run through the gel (lane 4).

The figure shows that transformant a2 correctly incorporated the synthetic gene of thaumatin II in its genome. Therefore, it was analyzed in greater detail to see if it expressed and secreted thaumatin II correctly. For immunoblotting analysis (Western-Blot) of the recombinant thaumatin, the methods described in section (1.4.2.) were used with the following modifications.

The experiment was started with 1 liter of a2 strain of *Penicillium roquefortii* which was grown for 8 days at 28° C. in a semi-defined medium for mycelium production (MSDPM). After vacuum filtration with a Büchner funnel, producing 45 g of mycelium per liter of culture, both the culture medium (liquid fraction) and the retained mycelium (solid fraction, 4.5 g) were analyzed.

The solid fraction was processed using the methods outlined in section (1.4.2.1), including sonication, thus obtaining 13.5 mL of mycelium extract in sonication solution. The 13.5 mL of mycelium extract and 10 mL of culture medium were precipitated with 10% trichloracetic acid and the precipitated material was resuspended in a final volume of 200 μL of sonication solution. These samples were then analyzed by protein electrophoreses and immunoblotting as described in detail in Example 1, section (1.4.2).

Figure 11:
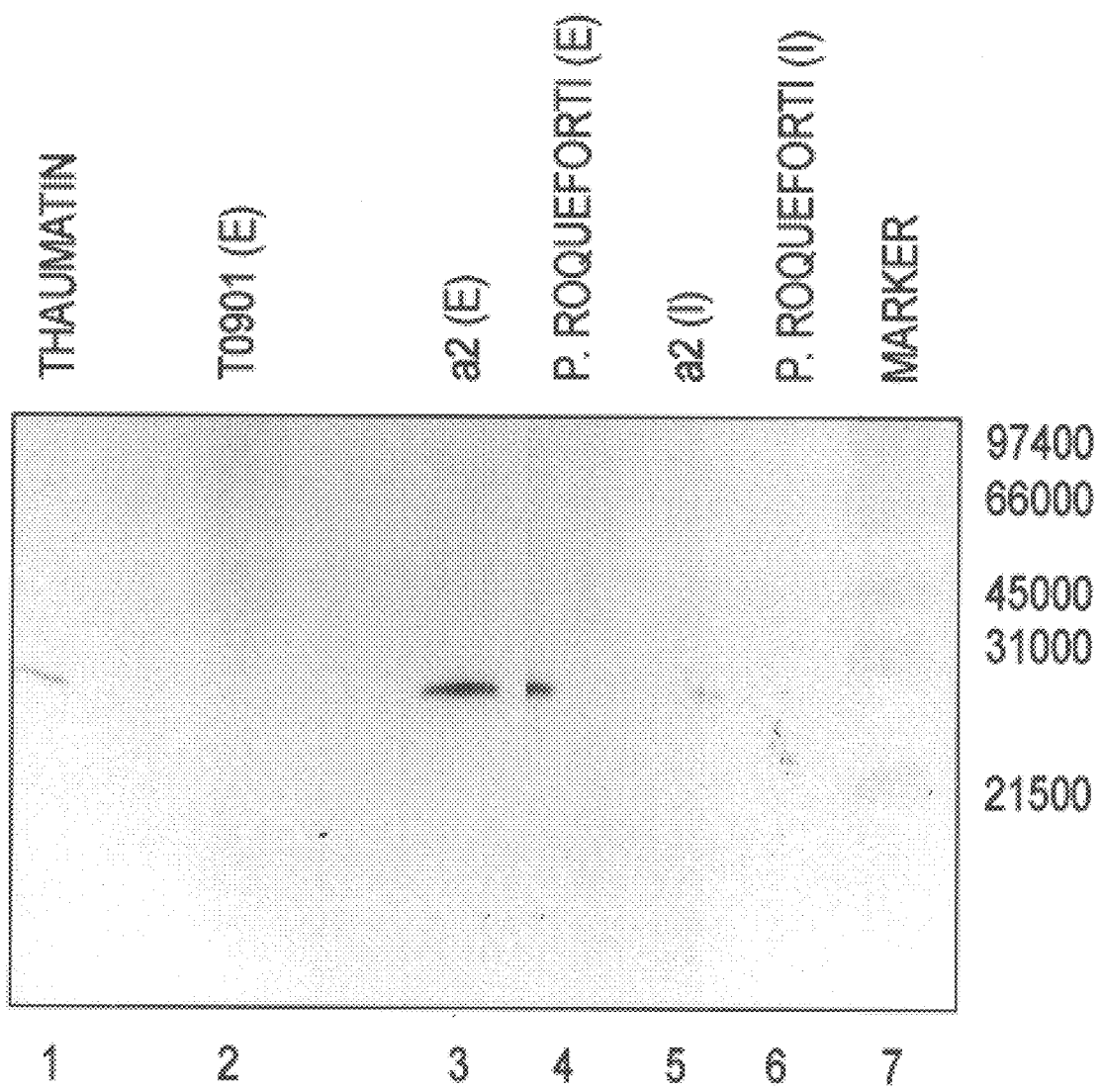

The results of this experiment are shown in FIG. 11 (14% SDS-polyacrylamide gel). Lane 7 in this figure contains proteins of known molecular weight (markers). The molecular weight corresponding to each protein is listed on the right of the figure. Lane 2 contains a sample of culture medium where fungus T0901 was grown. As described in Example 1, this fungus is a producer of intracellular thaumatin. Lanes 3 and 5 contain samples of culture medium (E for extracellular) and mycelium (I for intracellular) corresponding to transformant a2. Lanes 4 and 6 contain the same samples (E and I) corresponding to untransformed *Penicillium roquefortii*. As is clearly seen in FIG. 11, transformant a2 turned out to be a good producer and secretor of thaumatin. However, the effectiveness of the secretion was not complete given that a part of the thaumatin produced was not secreted, as is seen in the comparison between lanes 3 and 5. Organoleptic tests were performed on the culture broth and the characteristic sweet taste of thaumatin was detected.

Example 3

Extracellular Production Of Thaumatin In Aspergillus Niger Var. Awamori

Strain NRRL312 of *Aspergillus niger* var. *awamori* was transformed in the presence of polyethylene glycol, as described in the literature (Yelton et al., *Proc. Natl. Acad. Sci. USA,* 1984, vol. 81, pp. 1470–4), with some modifications as follows.

Four hundred mL of CM medium (malt extract, 5 g/L; yeast extract, 5 g/L; glucose, 5 g/L) in a 2-liter flask was inoculated with spores of *Aspergillus niger* var. *awamori* from a dish. The fungus grew for 16 hours. The mycelium was collected by filtration through a sterile gauze and washed with 100 mL of wash buffer (0.6M $MgSO_4$, 10 mM $Na_3PO_4$, pH 5.8). The mycelium was pressed in sterile paper towels and produced 2.5 grams.

For the formation of protoplasts, the mycelium was resuspended in 15 mL/g of cold protoplast buffer (1.2M $MgSO_4$, 10 mM $Na_3PO_4$, pH 5.8). At this point, 40 mg of Lysin enzyme (Sigma) was added per g of mycelium and the mixture was placed in ice for five minutes. After this incubation, 1 mL of BSA solution was added (12 mg/mL in protoplast buffer) and the solution was incubated for 3 or 4 hours at 30° C. Protoplast formation was monitored using a microscope. The mixture was filtered through nylon or a glass membrane and washed with the protoplast buffer. The protoplasts were centrifuged at 2000 rpm at 4° C. for 15 minutes with a floating rotor (Beckman GPR centrifuge). The protoplasts were resuspended in 15 mL of ST solution (1M sorbitol, 10 mM Tris-HCl, pH 7.5), centrifuged again and resuspended in 1 mL of ST. The solution was centrifuged again and washed twice with 1 mL of STC (ST plus 0.01M $CaCl_2$). The protoplasts were counted under the microscope, centrifuged again and resuspended in sufficient volume of STC to obtain a concentration of $10^8$ protoplasts/mL. Each 400-mL culture generally produced $10^8$ protoplasts. At that point, the protoplasts were directly plated in regeneration medium, in 5-mL tubes of 0.7% soft agar with saccharose osmotic stabilizer (1M), and were plated in basal medium with 1.5% agar.

For the transformation experiments, 200 µL of the $10^8$-protoplasts/mL protoplast solution was used to start. Ten µg of transformant DNA (pThIII in this case) and 50 µL of PTC (60% PEG 6000; 10 mM Tris-HCl, pH 7.5; 10 mM $CaCl_2$) were added to the protoplasts and the solution was incubated in ice for 20 minutes. One mL of PTC was then added and the solution was mixed well and kept at room temperature for five minutes. The protoplasts were centrifuged and resuspended in 200 µL of STC medium. The mixture was plated in regeneration medium with sulfanilamide at 1 mg/mL. The dishes were incubated upside down at 30° C. Regeneration was observed after three or four days of incubation.

(3.1) Preparation of the Regeneration Medium

1. Trace solution: 400 mg/L $CuSO_4.5H_2O$; 800 mg/L $FeSO_4.7H_2O$; 800 mg/L $MnSO_4.2H_2O$; 800 mg/L $Na_2MoO_4.2H_2O$; 40 mg/L $Na_2BrO_7.10H_2O$; 8 mg/L $ZnSO_4.7H_2O$.

2. Salt solution (50×): 26 g/L KCl; 26 g/L $MgSO_4.7H_2O$; 76 g/L $KH_2PO_4$; 50 mL/L of trace solution.

3. Ammonium tartrate: 30 grams per liter.

4. MMA (minimum Aspergillus medium): 10 or 15 g of glucose, or 7 g of agar was added to 970 mL of distilled water (final concentrations of 1.5% or 0.76%, respectively). The mixture was autoclaved and 10 mL of sterile ammonium tartrate solution and 20 mL of sterile salt solution were then added. Finally, the regeneration medium was prepared by adding saccharose to the MMA medium until the concentration of 1M was reached.

Example IV

Production, Secretion and Processing of a Glucoamylase-Thaumatin Fusion Protein

Figure 12:
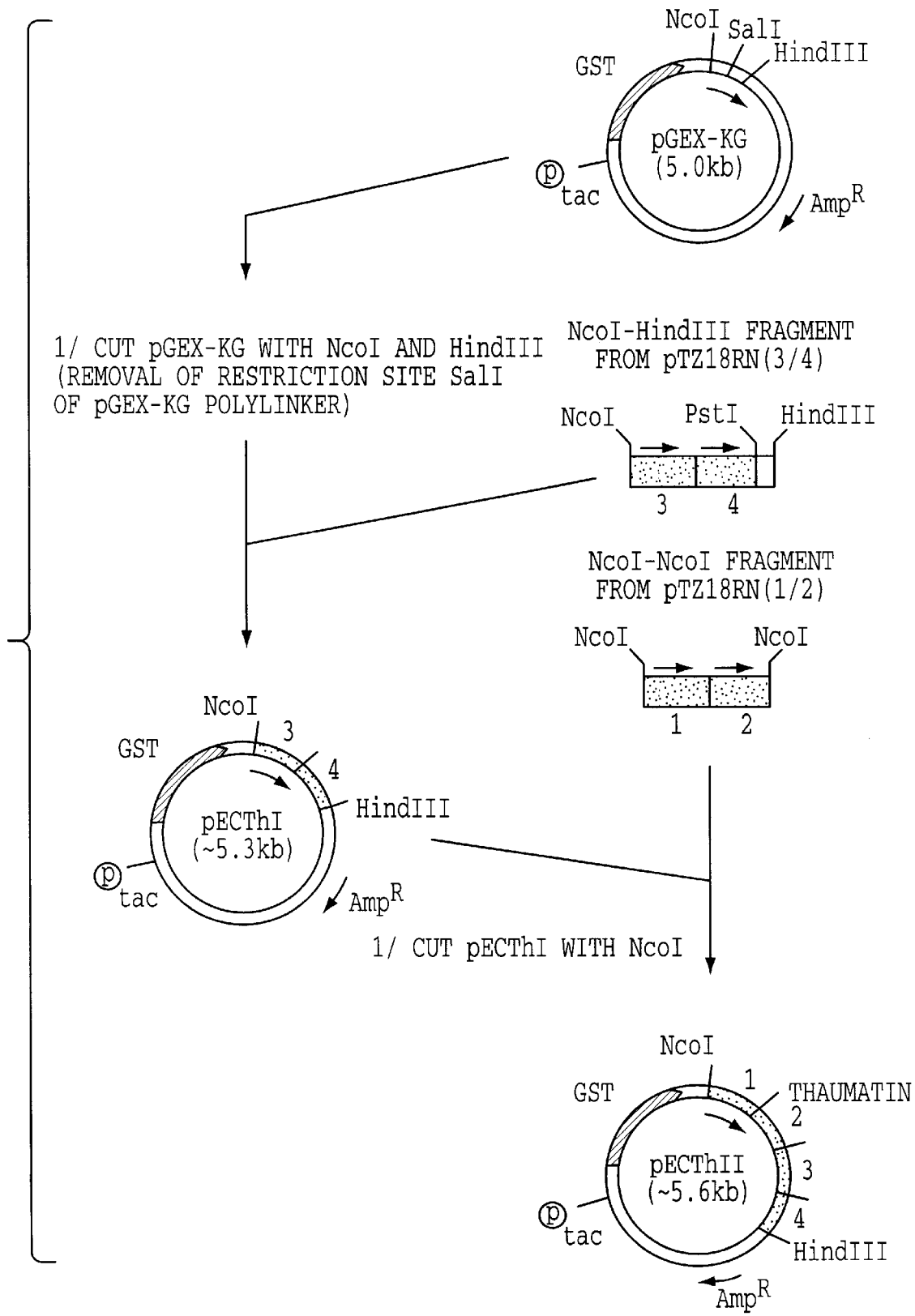
Figure 13A:
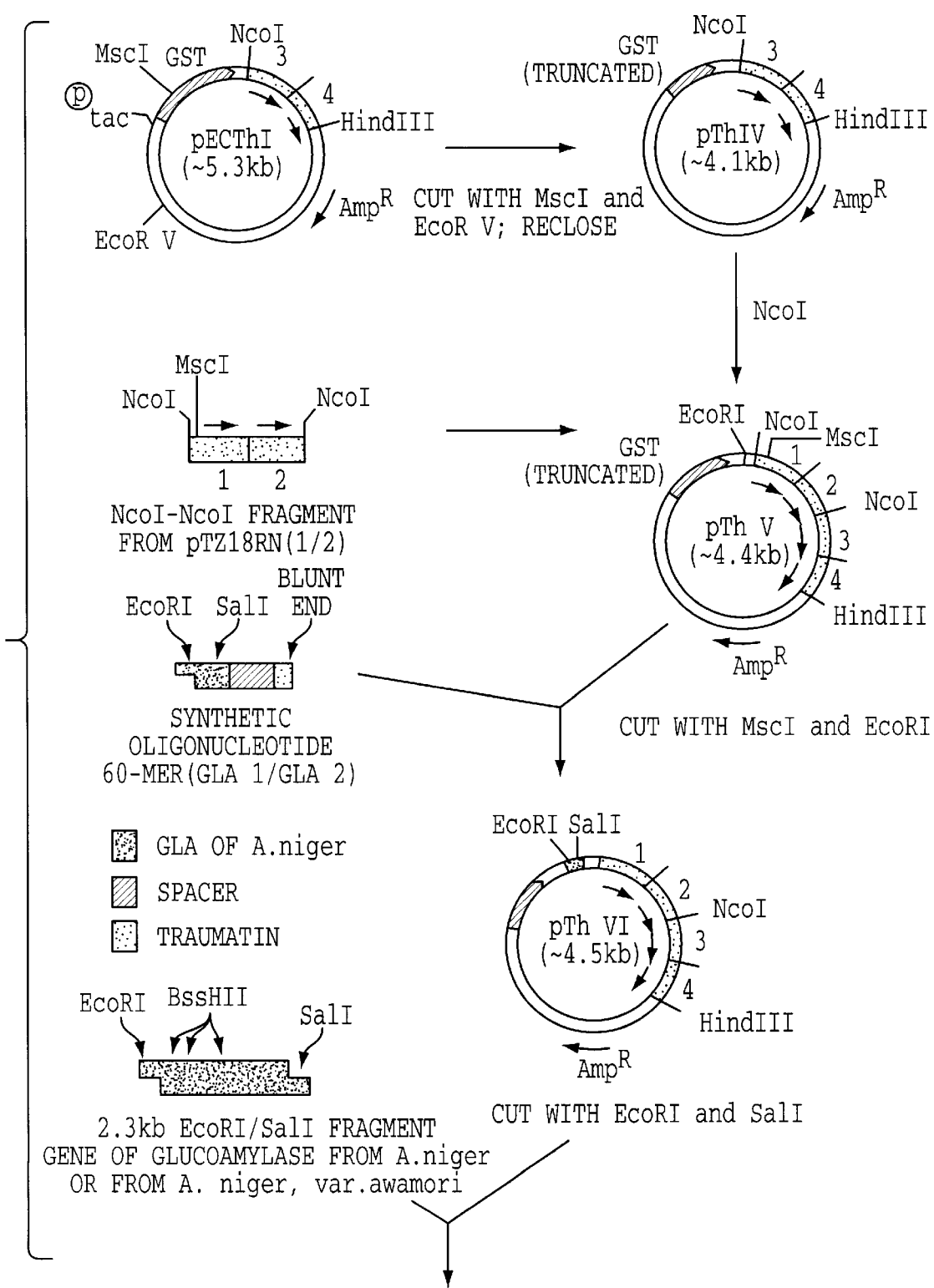
Figure 13B:
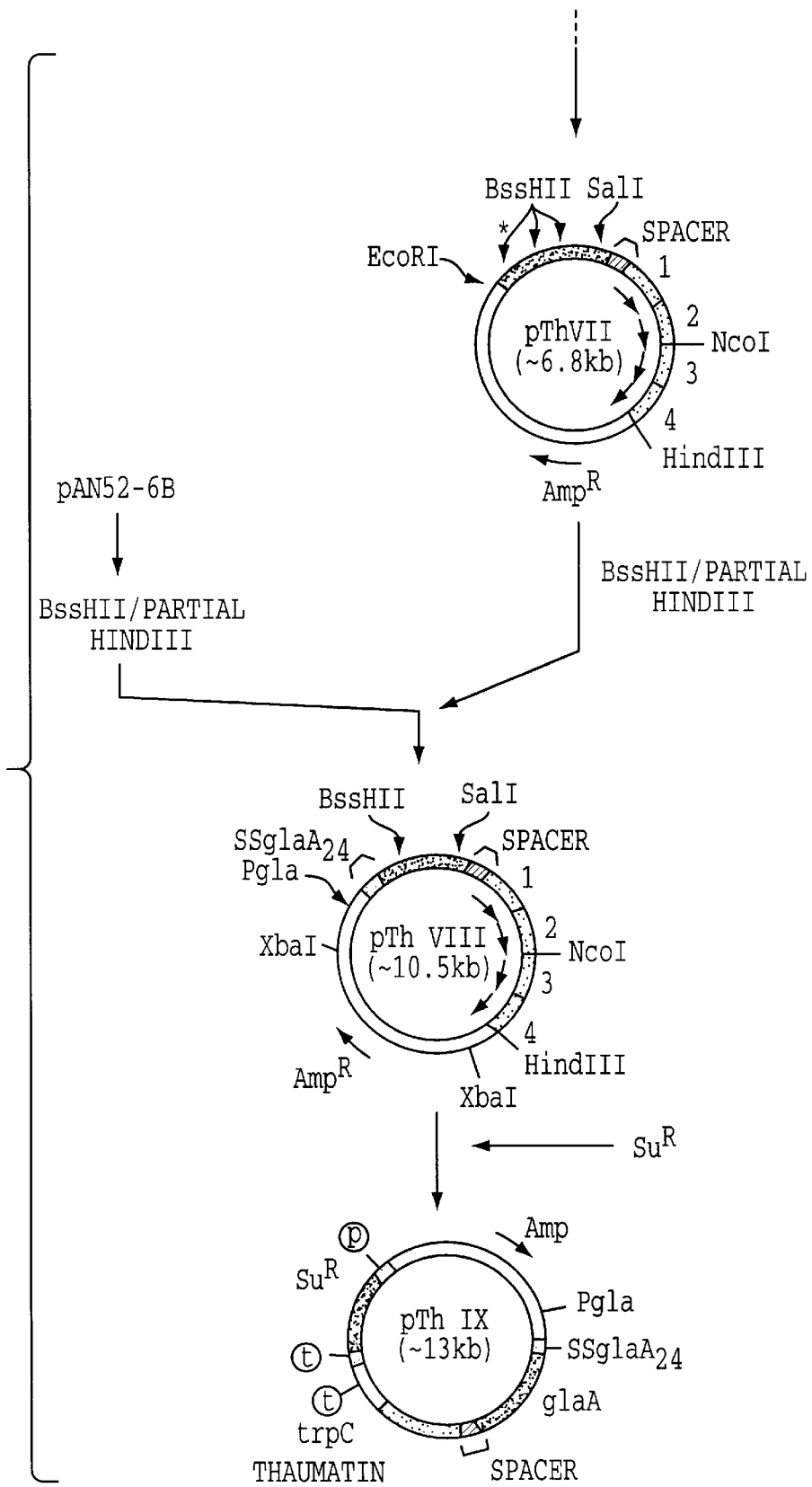

As outlined in FIG. 12, the pGEX-KG plasmid (5.0 Kb) (Pharmacia Biotech) was sequentially treated with NcoI and Hind III, thus generating a fragment of approximately 4900 bp. This fragment, which no longer contained the SalI restriction site of the pGEX-KG polylinker, was purified in a 0.8% agarose gel.

The previous fragment was ligated with a NcoI-HindIII fragment from plasmid pTZ18RN(¾) which contained the second part of the synthetic gene of thaumatin, thus generating plasmid pECThI (of approximately 5.3 Kb). This new plasmid was treated with NcoI and the linearized fragment was ligated with a NcoI-NcoI fragment from plasmid pTZ18RN(½), which contained the first part of the synthetic gene of thaumatin, thus generating plasmid pECThII (of approximately 5.6 Kb). Plasmid pECThII contained the synthetic gene of thaumatin under the control of the tac promoter of *Escherichia coli*. This construction made it possible to obtain intracellular production of recombinant thaumatin in *Escherichia coli*.

The starting point for the construction of pThIX was the pECThI plasmid (approximately 5.3 Kb). To eliminate the only MscI restriction site present in this plasmid, pECThI was sequentially treated with MscI and EcoRV (enzymes which produce blunt ends), thus releasing two fragments of 4.1 Kb and 1.2 Kb. The 4.1-Kb fragment was purified in a 0.8% agarose gel and religated with DNA ligase. The result was plasmid pThIV. This plasmid was linearized with NcoI and the linear fragment was ligated with a NcoI-NcoI fragment from plasmid pTZ18RN(½), which contained the first half of the synthetic gene of thaumatin, thus generating plasmid pThV.

The single-stranded oligonucleotides, GLA1 and GLA2, were commercially bought (Ingenasa S.A) and have the following sequences (included in those of FIG. 14):

```
GLA1:  5' AATTCTGCGGAACGTCGACCGCGACGG    SEQ ID NO:17
          TGACTGACACCTGGCGGCGAATGGATAAAAGGG-3'

GLA2:  5' CCCTTTTATCCATTCGCCGCCAGGTG     SEQ ID NO:18
          TCAGTCACCGTCGCGGTCGACGTTCCGCAG-3'
```

Figure 14:
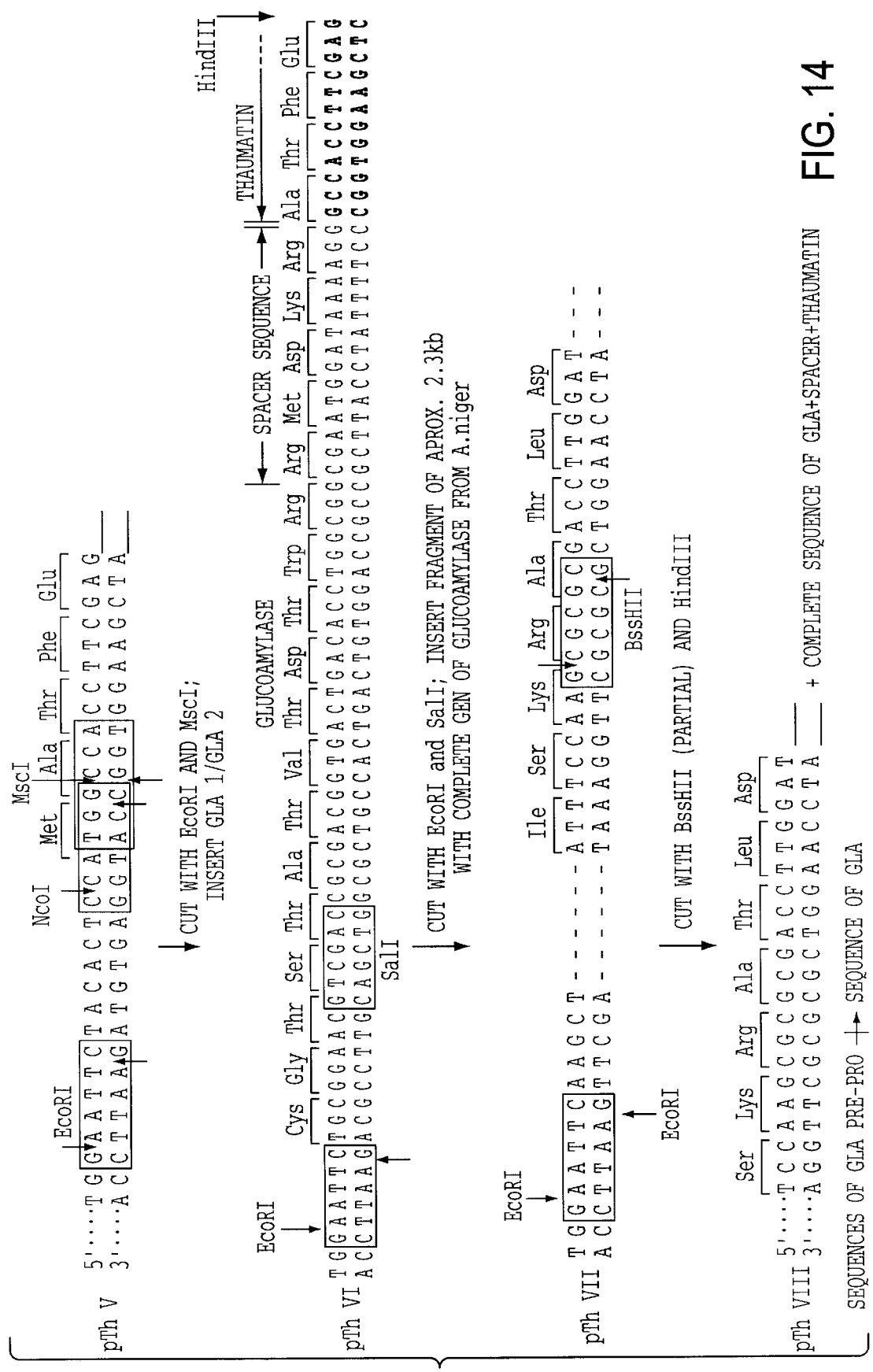

These two oligonucleotides were annealed as follows: 10 µg of each oligonucleotide was mixed in ligation buffer (40 mM Tris-HCl, pH 7.5; 20 mM $MgCl_2$; 50 mM NaCl) in a final volume of 25 µL. The mixture was heated for 5 minutes at 65° C. and the temperature was allowed to drop slowly (for one half hour) to 30° C. The double-stranded DNA annealed in this way was purified in 8% polyacrylamide gel. This double-stranded synthetic oligonucleotide, called GLA(½), had one blunt edge and one EcoRI end. Plasmid pThV was digested with MscI and EcoRI and ligated with the GLA(½) synthetic fragment, thus generating pThVI. FIG. 14 shows the connection between the last sequences of the glucoamylase gene of *Aspergillus niger*, the spacer sequence and the synthetic gene of thaumatin II.

The next step was to insert the complete gene of glucoamylase (glaA) of *Aspergillus niger* or *Aspergillus niger* var. *awamori,* respectively, in phase with the complete gene of thaumatin II so that a glucoamylase-thaumatin fusion protein could be formed.

Plasmid pFGA2, obtained from the Belgian collection of cultures and LMBP plasmids (Ghent, Belgium, number 1728), contained the complete gene of glucoamylase (glaA) of *Aspergillus niger*. The plasmid was digested with EcoRI and SalI, and a fragment of approximately 2.3 Kb was isolated containing the complete gene of glucoamylase except for the last 10 amino acids of the protein. This fragment was ligated with plasmid pThVI which had previously been digested with EcoRI and SalI, thus generating plasmid pThVII (the junctions are described in FIG. 14).

To obtain the glucoamylase gene of *Aspergillus niger* var. *awamori*, the following process was followed: total DNA of the NRRL312 strain of this fungus was prepared according to the protocol in section (1.4.1.1). Two oligonucleotides, complementary to the 5' and 3' ends of the glucoamylase gene were used to amplify the complete gene. The fragment thus amplified was purified in a 0.8% agarose gel and digested with EcoRI and SalI. This 2.3-Kb EcoRI-SalI fragment was subcloned in pBluescript SK (Stratagene Inc.), which had previously been treated with EcoRI and SalI, thus generating the pGLA-Aw plasmid.

In order to place the glucoamylase-spacer-thaumatin cassette under the control of the gla promoter of *Aspergillus niger*, the pThVII plasmid was digested with the restriction enzymes BssHII (partial digestion) and HindIII, and a fragment of approximately 3.0 Kb was isolated. This fragment was ligated with pAN52-6B which had previously been digested with BssHII and HindIII, thus obtaining plasmid pThVIII. Finally, the sulfanilamide resistance gene ($Su^R$) was inserted as described in Example 2, thus generating pThIX.

Plasmid pThIX contained: (i) a sulfanilamide resistance marker; (ii) a DNA sequence which encodes a fusion protein formed by (a) the synthetic gene of thaumatin II, (b) a spacer sequence which in turn contains a KEX2 processing sequence, and (c) the complete glucoamylase gene of *Aspergillus niger*; and finally, (iii) the signal sequence ("pre") and the "pro" sequence of the glucoamylase gene (glaA) of *Aspergillus niger*.

Plasmid pThIX was used to transform *Aspergillus niger* var. *awamori* as per the protocols specified in Example 3. Transformants which correctly secreted and processed thaumatin were obtained, and it was determined that the protein was sweet. In the same way, but using the pGLA-Aw plasmid instead of the pThVII plasmid, an analogue plasmid of pThIX was obtained containing the gla sequence of *A. awamori* instead of that of *A. niger*. Similarly, this plasmid was also used to transform a strain of *A. awamori*, with similar results.

LIST OF SEQUENCES

```
GCC ACC TTC GAG ATC GTC AAC CGC TGC TCC TAC ACC GTG TGG GCG GCC    48
Ala Thr Phe Glu Ile Val Asn Arg Cys Ser Tyr Thr Val Trp Ala Ala
1               5                   10                  15

GCC TCC AAA GGC GAC GCC GCC CTG GAC GCC GGC GGC CGC CAG CTC AAC    96
Ala Ser Lys Gly Asp Ala Ala Leu Asp Ala Gly Gly Arg Gln Leu Asn
            20                  25                  30

TCG GGA GAG TCC TGG ACC ATC AAC GTA GAA CCC GGC ACC AAG GGT GGC   144
Ser Gly Glu Ser Trp Thr Ile Asn Val Glu Pro Gly Thr Lys Gly Gly
        35                  40                  45

AAA ATC TGG GCC CGC ACC GAC TGC TAT TTC GAC GAC AGC GGC CGC GGC   192
Lys Ile Trp Ala Arg Thr Asp Cys Tyr Phe Asp Asp Ser Gly Arg Gly
    50                  55                  60

ATC TGC CGG ACC GGC GAC TGC GGC GGC CTC CTC CAG TGC AAG CGC TTC   240
Ile Cys Rag Thr Gly Asp Cys Gly Gly Leu Leu Gln Cys Lys Arg Phe
65                  70                  75                  80

GGC CGG CCG CCC ACC ACG CTG GCG GAG TTC TCG CTC AAC CAG TAC GGC   288
Gly Arg Pro Pro Thr Thr Leu Ala Glu Phe Ser Leu Asn Gln Tyr Gly
                85                  90                  95

AAG GAC TAC ATC GAC ATC TCC AAC ATC AAA GGC TTC AAC GTG CCG ATG   336
Lys Asp Tyr Ile Asp Ile Ser Asn Ile Lys Gly Phe Asn Val Pro Met
            100                 105                 110

GAC TTC AGC CCG ACC ACG CGC GGC TGC CGC GGG GTG CGG TGC GCC GCC   384
Asp Phe Ser Pro Thr Thr Arg Gly Cys Arg Gly Val Arg Cys Ala Ala
        115                 120                 125

GAC ATC GTG GGG CAG TGC CCG GCG AAG CTG AAG GCG CCG GGG GGT GGT   432
Asp Ile Val Gly Gln Cys Pro Ala Lys Leu Lys Ala Pro Gly Gly Gly
    130                 135                 140

TGC AAC GAT GCG TGC ACC GTG TTC CAG ACG AGC GAG TAC TGC TGC ACC   480
Cys Asn Asp Ala Cys Thr Val Phe Gln Thr Ser Glu Tyr Cys Cys Thr
145                 150                 155                 160

ACG GGG AAG TGC GGG CCG ACG GAG TAC TCG CGC TTC TTC AAG AGG CTT   528
Thr Gly Lys Cys Gly Pro Thr Glu Tyr Ser Arg Phe Phe Lys Arg Leu
                165                 170                 175

TGC CCG GAC GCG TTC AGT TAT GTC CTG GAC AAG CCA ACC ACC GTC ACC   576
Cys Pro Asp Ala Phe Ser Tyr Val Leu Asp Lys Pro Thr Thr Val Thr
            180                 185                 190

TGC CCC GGC AGC TCC AAC TAC AGG GTC ACT TTC TGC CCT ACT GCC(TAA)n 624
Cys Pro Gly Ser Ser Asn Tyr Arg Val Thr Phe Cys Pro Thr Ala
        195                 200                 205
```

Amino-acid sequence SEQ ID NO:2 of the protein thaumatin II, and nucleotide sequence SEQ ID NO:1 of the natural gene.

```
GCC ACC TTC GAG ATC GTC AAC CGC TGC TCC TAC ACC GTC TGG GCC GCC    48
Ala Thr Phe Glu Ile Val Asn Arg Cys Ser Tyr Thr Val Trp Ala Ala
1               5                   10                  15

GCC TCC AAG GGC GAC GCC GCC CTC GAC GCC GGC GGC CGC CAG CTC AAC    96
Ala Ser Lys Gly Asp Ala Ala Leu Asp Ala Gly Gly Arg Gln Leu Asn
            20                  25                  30

TCC GGC GAG TCC TGG ACC ATC AAC GTC GAG CCC GGC ACC AAG GGC GGC   144
Ser Gly Glu Ser Trp Thr Ile Asn Val Glu Pro Gly Thr Lys Gly Gly
        35                  40                  45

AAG ATC TGG GCC CGC ACC GAC TGC TAC TTC GAC GAC TCC GGC CGC GGC   192
Lys Ile Trp Ala Arg Thr Asp Cys Try Phe Asp Asp Ser Gly Arg Gly
    50                  55                  60

ATC TGC CGC ACC GGC GAC TGC GGC GGC CTC CTC CAG TGC AAG CGC TTC   240
Ile Cys Rag Thr Gly Asp Cys Gly Gly Leu Leu Gln Cys Lys Arg Phe
65                  70                  75                  80

GGC CGC CCC CCC ACC ACC CTC GCC GAC TTC TCC CTC AAC CAG TAC GGC   288
Gly Arg Pro Pro Thr Thr Leu Ala Glu Phe Ser Leu Asn Gln Tyr Gly
                85                  90                  95

AAG GAC TAC ATC GAC ATC TCC AAC ATC AAG GGC TTC AAC GTC CCC ATG   336
Lys Asp Tyr Ile Asp Ile Ser Asn Ile Lys Gly Phe Asn Val Pro Met
            100                 105                 110

GAC TTC TCC CCC ACC ACC CGC GGC TGC CGC GGG GTC CGC TGC GCC GCC   384
Asp Phe Ser Pro Thr Thr Arg Gly Cys Arg Gly Val Arg Cys Ala Ala
        115                 120                 125

GAC ATC GTC GGC CAG TGC CCC GCC AAG CTC AAG GCC CCC GGC GGC GGC   432
Asp Ile Val Gly Gln Cys Pro Ala Lys Leu Lys Ala Pro Gly Gly Gly
    130                 135                 140

TGC AAC GAC GCC TGC ACC GTC TTC CAG ACC TCC GAG TAC TGC TGC ACC   480
Cys Asn Asp Ala Cys Thr Val Phe Gln Thr Ser Glu Tyr Cys Cys Thr
145                 150                 155                 160

ACC GGC AAG TGC GGC CCC ACC GAG TAC TCC CGC TTC TTC AAG CGC CTC   528
Thr Gly Lys Cys Gly Pro Thr Glu Tyr Ser Arg Phe Phe Lys Arg Leu
                165                 170                 175

TGC CCC GAC GCC TTC TCC TAC GTC CTC GAC AAG CCC ACC ACC GTC ACC   576
Cys Pro Asp Ala Phe Ser Tyr Val Leu Asp Lys Pro Thr Thr Val Thr
            180                 185                 190

TGC CCC GGC TCC TCC AAC TAC CGC GTC ACC TTC TGC CCC ACC GCC(TAA)n 624
Cys Pro Gly Ser Ser Asn Tyr Arg Val Thr Phe Cys Pro Thr Ala
        195                 200                 205
```

Amino-acid sequence SEQ ID NO:4 of thaumatin II and nucleotide sequence SEQ ID NO:3 of the artificial, synthetic and completely optimized gene, used in the examples of this invention, to which the n codons with TAA termination (n≧1) were added.

We claim:

1. An optimized DNA comprising a DNA which encodes thaumatin II, wherein more than 50% of codons which are not preferred codons in naturally occurring thaumatin II gene, as shown by SEQ ID NO:1, are preferred codons in said optimized DNA, wherein said preferred codons are:

Ala(GCC), Arg(CGC), Asn(AAC), Asp(GAC), Cys(TGC), Lys(AAG), Gln(CAG), Glu(GAG), Gly(GGC), Ile(ATC), Leu(CTC), Met(ATG), Phe(TTC), Pro(CCC), Ser(TCC), Thr(ACC), Trp(TGG), Tyr(TAC), Val(GTC).

2. The optimized DAN of claim 1 wherein more than 75% of codons which are not preferred codons in SEQ ID NO:1 are preferred codons in said optimized DNA.

3. The DNA of Sequence ID No. 3.

4. An expression vector comprising: (i) an optimized DNA according to claim 1, 2 or 3, under the control of an expression cassette for filamentous fungi, said expression cassette comprising a promoter sequence and a termination sequence operative in filamentous fungi; (ii) a selection marker; and, optionally, (iii) a secretion signal sequence for promoting extracellular secretion of thaumatin.

5. An expression vector according to claim 4 wherein the promoter sequence is a promoter sequence of an *Aspergillus niger* glyceraldehyde 3-phosphate dehydrogenase or glucoamylase gene; the termination sequence is a termination sequence of *Aspergillus nidulans* tryptophan C gene; and the selection marker is a sulfanilamide resistance marker.

6. An expression vector capable of directing expression of a thaumatin-glucoamylase fusion protein in filamentous fungi, wherein said expression vector comprises: (i) a selection marker; (ii) a DNA comprising said optimized DNA according to claim 1, 2 or 3, linked to a spacer sequence which comprises a KEX2 processing sequence and to a glucoamylase gene of *Aspergillus niger* or *Aspergillus niger* var. *awamori*; and (iii) a "pre" signal sequence and a "pro" sequence of said glucoamylase gene.

7. A filamentous fungus capable of producing thaumatin II, wherein said filamentous fungus has been transformed with an expression vector of claim 4.

8. A filamentous fungus capable of producing thaumatin II, wherein said filamentous fungus has been transformed with an expression vector of claim 5.

9. A filamentous fungus capable of producing thaumatin II, wherein said filamentous fungus has been transformed with an expression vector of claim 6.

10. A culture comprising the filamentous fungus of claim 7 wherein said filamentous fungus is a species selected from the group consisting of *Penicillium roquefortii, Aspergillus niger*, and *Aspergillus niger* var. *awamori*.

11. A culture comprising the filamentous fungus of claim 8 wherein said filamentous fungus is a species selected from the group consisting of *Penicillium roquefortii, Aspergillus niger*, and *Aspergillus niger* var. *awamori*.

12. A culture comprising the filamentous fungus of claim 9 wherein said filamentous fungus is a species selected from the group consisting of *Penicillium roquefortii, Aspergillus niger*, and *Aspergillus niger* var. *awamori*.

13. A process for producing thaumatin II, wherein said process comprises the steps of: (i) transforming a strain of filamentous fungus with an expression vector of claim 4 to produce a transformed filamentous fungus, (ii) culturing the transformed filamentous fungus under conditions wherein thaumatin II is expressed and, optionally, (iii) recovering the thaumatin II.

14. A process according to claim 13 wherein the filamentous fungus is a species selected from the group consisting of *Penicillium roquefortii, Aspergillus niger*, and *Aspergillus niger* var. *awamori*.

15. An optimized DNA comprising a DNA which encodes thaumatin I, wherein more than 50% of codons which are not preferred codons in naturally occurring thaumatin I gene are preferred codons in said optimized DNA, wherein said preferred codons are:

Ala(GCC), Arg(CGC), Asn(AAC), Asp(GAC), Cys(TGC), Lys(AAG), Gln(CAG), Glu(GAG), Gly(GGC), Ile(ATC), Leu(CTC), Met(ATG), Phe(TTC), Pro(CCC), Ser(TCC), Thr(ACC), Trp(TGG), Tyr(TAC), Val(GTC).

16. The optimized DNA of claim 15 wherein more than 75% of codons which are not preferred codons in naturally occurring thaumatin I DNA are preferred codons in said optimized DNA.

17. An optimized DNA encoding thaumatin I, wherein said DNA comprises a sequence of Sequence ID No. 3 with the following substitutions: C in place of G at nucleotide 138, T in place of C at nucleotide 187, C in place of G at nucleotide 188, A in place of C at nucleotide 199, A in place of G at nucleotide 200, G in place of C at nucleotide 201, G in place of A at nucleotide 227, C in place of G at nucleotide 228, and A in place of G at nucleotide 337.

18. An expression vector comprising: (i) an optimized DNA according to claim 15, 16 or 17, under the control of an expression cassette for filamentous fungi, said expression cassette comprising a promoter sequence and a termination sequence operative in filamentous fungi; (ii) a selection marker; and, optionally, (iii) a secretion signal sequence for promoting extracellular secretion of thaumatin.

19. An expression vector according to claim 18 wherein the promoter sequence is a promoter sequence of an *Aspergillus niger* glyceraldehyde 3-phosphate dehydrogenase or glucoamylase gene; the termination sequence is a termination sequence of *Aspergillus nidulans* tryptophan C gene; and the selection marker is a sulfanilamide resistance marker.

20. An expression vector capable of directing expression of a thaumatin-glucoamylase fusion protein in filamentous fungi, wherein said expression vector comprises: (i) a selection marker; (ii) a DNA comprising said optimized DNA according to claim 15, 16 or 17 linked to a spacer sequence which comprises a KEX2 processing sequence and to a glucoamylase gene of *Aspergillus niger* or of *Aspergillus niger* var. *awamori;* and (iii) a "pre" signal sequence and a "pro" sequence of said glucoamylase gene.

21. A filamentous fungus capable of producing thaumatin I, wherein said filamentous fungus has been transformed with the expression vector of claim 18.

22. A filamentous fungus capable of producing thaumatin I, wherein said filamentous fungus has been transformed with the expression vector of claim 19.

23. A filamentous fungus capable of producing thaumatin I, wherein said filamentous fungus has been transformed with the expression vector of claim 20.

24. A culture comprising the filamentous fungus of claim 21 wherein said filamentous fungus is a species selected from the group consisting of *Penicillium roquefortii, Aspergillus niger,* and *Aspergillus niger* var. *awamori.*

25. A culture comprising the filamentous fungus of claim 22 wherein said filamentous fungus is a species selected from the group consisting of *Penicillium roquefortii, Aspergillus niger,* and *Aspergillus niger* var. *awamori.*

26. A culture comprising the filamentous fungus of claim 23 wherein said filamentous fungus is a species selected from the group consisting of *Penicillium roquefortii, Aspergillus niger,* and *Aspergillus niger* var. *awamori.*

27. A process for producing thaumatin I, wherein said process comprises the steps of: (i) transforming a strain of filamentous fungus with an expression vector of claim 18 to produce a transformed filamentous fungus, (ii) culturing the transformed filamentous fungus under conditions wherein thaumatin I is expressed and, optionally, (iii) recovering the thaumatin I.

28. A process according to claim 27 wherein the filamentous fungus is a species selected from the group consisting of *Penicillium roquefortii, Aspergillus niger,* and *Aspergillus niger* var. *awamori.*

29. The optimized DNA of claim 1 further comprising one or more stop codons selected from TAA, TAG and TGA.

30. The optimized DNA of claim 15 wherein said DNA further comprises one or more stop codons selected from TAA, TAG and TGA.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 624 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 1..621

(xi) SEQUENCE DESCRIPTION: SEQ ID NO:1:

```
GCC ACC TTC GAG ATC GTC AAC CGC TGC TCC TAC ACC GTG TGG GCG GCC         48
Ala Thr Phe Glu Ile Val Asn Arg Cys Ser Tyr Thr Val Trp Ala Ala
 1               5                  10                  15

GCC TCC AAA GGC GAC GCC GCC CTG GAC GCC GGC GGC CGC CAG CTC AAC         96
Ala Ser Lys Gly Asp Ala Ala Leu Asp Ala Gly Gly Arg Gln Leu Asn
                20                  25                  30

TCG GGA GAG TCC TGG ACC ATC AAC GTA GAA CCC GGC ACC AAG GGT GGC        144
Ser Gly Glu Ser Trp Thr Ile Asn Val Glu Pro Gly Thr Lys Gly Gly
            35                  40                  45

AAA ATC TGG GCC CGC ACC GAC TGC TAT TTC GAC GAC AGC GGC CGC GGC        192
Lys Ile Trp Ala Arg Thr Asp Cys Tyr Phe Asp Asp Ser Gly Arg Gly
        50                  55                  60

ATC TGC CGG ACC GGC GAC TGC GGC GGC CTC CTC CAG TGC AAG CGC TTC        240
Ile Cys Arg Thr Gly Asp Cys Gly Gly Leu Leu Gln Cys Lys Arg Phe
 65                 70                  75                  80

GGC CGG CCG CCC ACC ACG CTG GCG GAG TTC TCG CTC AAC CAG TAC GGC        288
Gly Arg Pro Pro Thr Thr Leu Ala Glu Phe Ser Leu Asn Gln Tyr Gly
                85                  90                  95

AAG GAC TAC ATC GAC ATC TCC AAC ATC AAA GGC TTC AAC GTG CCG ATG        336
Lys Asp Tyr Ile Asp Ile Ser Asn Ile Lys Gly Phe Asn Val Pro Met
                100                 105                 110

GAC TTC AGC CCG ACC ACG CGC GGC TGC CGC GGG GTG CGG TGC GCC GCC        384
Asp Phe Ser Pro Thr Thr Arg Gly Cys Arg Gly Val Arg Cys Ala Ala
            115                 120                 125

GAC ATC GTG GGG CAG TGC CCG GCG AAG CTG AAG GCG CCG GGG GGT GGT        432
Asp Ile Val Gly Gln Cys Pro Ala Lys Leu Lys Ala Pro Gly Gly Gly
        130                 135                 140

TGC AAC GAT GCG TGC ACC GTG TTC CAG ACG AGC GAG TAC TGC TGC ACC        480
Cys Asn Asp Ala Cys Thr Val Phe Gln Thr Ser Glu Tyr Cys Cys Thr
145                 150                 155                 160

ACG GGG AAG TGC GGG CCG ACG GAG TAC TCG CGC TTC TTC AAG AGG CTT        528
Thr Gly Lys Cys Gly Pro Thr Glu Tyr Ser Arg Phe Phe Lys Arg Leu
                165                 170                 175

TGC CCG GAC GCG TTC AGT TAT GTC CTG GAC AAG CCA ACC ACC GTC ACC        576
Cys Pro Asp Ala Phe Ser Tyr Val Leu Asp Lys Pro Thr Thr Val Thr
            180                 185                 190

TGC CCC GGC AGC TCC AAC TAC AGG GTC ACT TTC TGC CCT ACT GCC            621
Cys Pro Gly Ser Ser Asn Tyr Arg Val Thr Phe Cys Pro Thr Ala
        195                 200                 205
```

```
TAA                                                                    624
```

(2) INFORMATION FOR SEQ ID NO:2:

(i) SEQUENCE CHARACTERISTICS:
        (A) LENGTH: 207 amino acids
        (B) TYPE: amino acid
        (D) TOPOLOGY: linear (ii) MOLECULE TYPE: protein (xi) SEQUENCE DESCRIPTION: SEQ ID NO:2:

```
Ala Thr Phe Glu Ile Val Asn Arg Cys Ser Tyr Thr Val Trp Ala Ala
  1               5                  10                  15

Ala Ser Lys Gly Asp Ala Ala Leu Asp Ala Gly Gly Arg Gln Leu Asn
             20                  25                  30

Ser Gly Glu Ser Trp Thr Ile Asn Val Glu Pro Gly Thr Lys Gly Gly
         35                  40                  45

Lys Ile Trp Ala Arg Thr Asp Cys Tyr Phe Asp Asp Ser Gly Arg Gly
 50                  55                  60

Ile Cys Arg Thr Gly Asp Cys Gly Gly Leu Leu Gln Cys Lys Arg Phe
 65                  70                  75                  80

Gly Arg Pro Pro Thr Thr Leu Ala Glu Phe Ser Leu Asn Gln Tyr Gly
                 85                  90                  95

Lys Asp Tyr Ile Asp Ile Ser Asn Ile Lys Gly Phe Asn Val Pro Met
                100                 105                 110

Asp Phe Ser Pro Thr Thr Arg Gly Cys Arg Gly Val Arg Cys Ala Ala
            115                 120                 125

Asp Ile Val Gly Gln Cys Pro Ala Lys Leu Lys Ala Pro Gly Gly Gly
        130                 135                 140

Cys Asn Asp Ala Cys Thr Val Phe Gln Thr Ser Glu Tyr Cys Cys Thr
145                 150                 155                 160

Thr Gly Lys Cys Gly Pro Thr Glu Tyr Ser Arg Phe Phe Lys Arg Leu
                165                 170                 175

Cys Pro Asp Ala Phe Ser Tyr Val Leu Asp Lys Pro Thr Thr Val Thr
            180                 185                 190

Cys Pro Gly Ser Ser Asn Tyr Arg Val Thr Phe Cys Pro Thr Ala
        195                 200                 205
```

(2) INFORMATION FOR SEQ ID NO:3:

(i) SEQUENCE CHARACTERISTICS:
        (A) LENGTH: 624 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Optimized cDNA"

(iii) HYPOTHETICAL: NO (iv) ANTI-SENSE: NO (ix) FEATURE:
        (A) NAME/KEY: CDS
        (B) LOCATION: 1..621

(xi) SEQUENCE DESCRIPTION: SEQ ID NO:3:

```
GCC ACC TTC GAG ATC GTC AAC CGC TGC TCC TAC ACC GTC TGG GCC GCC      48
Ala Thr Phe Glu Ile Val Asn Arg Cys Ser Tyr Thr Val Trp Ala Ala
  1               5                  10                  15

GCC TCC AAG GGC GAC GCC GCC CTC GAC GCC GGC GGC CGC CAG CTC AAC      96
```

```
Ala Ser Lys Gly Asp Ala Ala Leu Asp Ala Gly Gly Arg Gln Leu Asn
             20                  25                  30

TCC GGC GAG TCC TGG ACC ATC AAC GTC GAG CCC GGC ACC AAG GGC GGC         144
Ser Gly Glu Ser Trp Thr Ile Asn Val Glu Pro Gly Thr Lys Gly Gly
             35                  40                  45

AAG ATC TGG GCC CGC ACC GAC TGC TAC TTC GAC GAC TCC GGC CGC GGC         192
Lys Ile Trp Ala Arg Thr Asp Cys Tyr Phe Asp Asp Ser Gly Arg Gly
             50                  55                  60

ATC TGC CGC ACC GGC GAC TGC GGC GGC CTC CTC CAG TGC AAG CGC TTC         240
Ile Cys Arg Thr Gly Asp Cys Gly Gly Leu Leu Gln Cys Lys Arg Phe
 65              70                  75                  80

GGC CGC CCC CCC ACC ACC CTC GCC GAG TTC TCC CTC AAC CAG TAC GGC         288
Gly Arg Pro Pro Thr Thr Leu Ala Glu Phe Ser Leu Asn Gln Tyr Gly
                     85                  90                  95

AAG GAC TAC ATC GAC ATC TCC AAC ATC AAG GGC TTC AAC GTC CCC ATG         336
Lys Asp Tyr Ile Asp Ile Ser Asn Ile Lys Gly Phe Asn Val Pro Met
                 100                 105                 110

GAC TTC TCC CCC ACC ACC CGC GGC TGC CGC GGC GTC CGC TGC GCC GCC         384
Asp Phe Ser Pro Thr Thr Arg Gly Cys Arg Gly Val Arg Cys Ala Ala
             115                 120                 125

GAC ATC GTC GGC CAG TGC CCC GCC AAG CTC AAG GCC CCC GGC GGC GGC         432
Asp Ile Val Gly Gln Cys Pro Ala Lys Leu Lys Ala Pro Gly Gly Gly
 130                 135                 140

TGC AAC GAC GCC TGC ACC GTC TTC CAG ACC TCC GAG TAC TGC TGC ACC         480
Cys Asn Asp Ala Cys Thr Val Phe Gln Thr Ser Glu Tyr Cys Cys Thr
145                 150                 155                 160

ACC GGC AAG TGC GGC CCC ACC GAG TAC TCC CGC TTC TTC AAG CGC CTC         528
Thr Gly Lys Cys Gly Pro Thr Glu Tyr Ser Arg Phe Phe Lys Arg Leu
                 165                 170                 175

TGC CCC GAC GCC TTC TCC TAC GTC CTC GAC AAG CCC ACC ACC GTC ACC         576
Cys Pro Asp Ala Phe Ser Tyr Val Leu Asp Lys Pro Thr Thr Val Thr
             180                 185                 190

TGC CCC GGC TCC TCC AAC TAC CGC GTC ACC TTC TGC CCC ACC GCC             621
Cys Pro Gly Ser Ser Asn Tyr Arg Val Thr Phe Cys Pro Thr Ala
         195                 200                 205

TAA                                                                     624

(2) INFORMATION FOR SEQ ID NO:4:

(i) SEQUENCE CHARACTERISTICS:
        (A) LENGTH: 207 amino acids
        (B) TYPE: amino acid
        (D) TOPOLOGY: linear (ii) MOLECULE TYPE: protein (xi) SEQUENCE DESCRIPTION: SEQ ID NO:4:

Ala Thr Phe Glu Ile Val Asn Arg Cys Ser Tyr Thr Val Trp Ala Ala
 1               5                  10                  15

Ala Ser Lys Gly Asp Ala Ala Leu Asp Ala Gly Gly Arg Gln Leu Asn
             20                  25                  30

Ser Gly Glu Ser Trp Thr Ile Asn Val Glu Pro Gly Thr Lys Gly Gly
             35                  40                  45

Lys Ile Trp Ala Arg Thr Asp Cys Tyr Phe Asp Asp Ser Gly Arg Gly
             50                  55                  60

Ile Cys Arg Thr Gly Asp Cys Gly Gly Leu Leu Gln Cys Lys Arg Phe
 65              70                  75                  80

Gly Arg Pro Pro Thr Thr Leu Ala Glu Phe Ser Leu Asn Gln Tyr Gly
                     85                  90                  95

Lys Asp Tyr Ile Asp Ile Ser Asn Ile Lys Gly Phe Asn Val Pro Met
```

```
              100                 105                 110
Asp Phe Ser Pro Thr Thr Arg Gly Cys Arg Gly Val Arg Cys Ala Ala
        115                 120                 125

Asp Ile Val Gly Gln Cys Pro Ala Lys Leu Lys Ala Pro Gly Gly Gly
130                 135                 140

Cys Asn Asp Ala Cys Thr Val Phe Gln Thr Ser Glu Tyr Cys Cys Thr
145                 150                 155                 160

Thr Gly Lys Cys Gly Pro Thr Glu Tyr Ser Arg Phe Phe Lys Arg Leu
                165                 170                 175

Cys Pro Asp Ala Phe Ser Tyr Val Leu Asp Lys Pro Thr Val Thr
        180                 185                 190

Cys Pro Gly Ser Ser Asn Tyr Arg Val Thr Phe Cys Pro Thr Ala
            195                 200                 205
```

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Multicloning site of
            pTZ18R"

(iii) HYPOTHETICAL: NO (xi) SEQUENCE DESCRIPTION: SEQ ID NO:5:

```
CCCGGGGATC CTCTAGAGTC GACCTGCAGG CAT                          33
```

(2) INFORMATION FOR SEQ ID NO:6:

(i) SEQUENCE CHARACTERISTICS:
        (A) LENGTH: 106 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:6:

```
AAATGGAGGA TCCATGGCCA CCTTCGAGAT CGTCAACCGC TGCTCCTACA CCGTCTGGGC    60

CGCCGCCTCC AAGGGCGACG CCGCCCTCGA CGCCGGCGGC CGCCAG                  106
```

(2) INFORMATION FOR SEQ ID NO:7:

(i) SEQUENCE CHARACTERISTICS:
        (A) LENGTH: 87 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:7:

```
GCGGGCCCAG ATCTTGCCGC CCTTGGTGCC GGGCTCGACG TTGATGGTCC AGGACTCGCC    60

GGAGTTGAGC TGGCGGCCGC CGGCGTC                                       87
```

(2) INFORMATION FOR SEQ ID NO:8:

(i) SEQUENCE CHARACTERISTICS:
        (A) LENGTH: 117 base pairs
        (B) TYPE: nucleic acid
        (C) STRANDEDNESS: double (D) TOPOLOGY: linear (ii) MOLECULE TYPE: other nucleic acid (xi) SEQUENCE DESCRIPTION: SEQ ID NO:8:

GGCGGCAAGA TCTGGGCCCG CACCGACTGC TACTTCGACG ACTCCGGCCG CGGCATCTGC    60

CGCACCGGCG ACTGCGGCGG CCTCCTCCAG TGCAAGCGCT TCGGCCGCCC CCCCACC    117

(2) INFORMATION FOR SEQ ID NO:9:

(i) SEQUENCE CHARACTERISTICS:
        (A) LENGTH: 103 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:9:

AGTCCATGGG GACGTTGAAG CCCTTGATGT TGGAGATGTC GATGTAGTCC TTGCCGTACT    60

GGTTGAGGGA GAACTCGGCG AGGGTGGTGG GGGGGCGGCC GAA    103

(2) INFORMATION FOR SEQ ID NO:10:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:10:

AACGTCCCCA TGGACTTCTC CCCCACCACC CGCGGCTGCC GCGGCGTCCG CTGCGCCGCC    60

GACATCGTCG GCCAGTGCCC CGCC    84

(2) INFORMATION FOR SEQ ID NO:11:

(i) SEQUENCE CHARACTERISTICS:
        (A) LENGTH: 64 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:11:

AGACGGTGCA GGCGTCGTTG CAGCCGCCGC CGGGGGCCTT GAGCTTGGCG GGGCACTGGC    60

CGAC    64

(2) INFORMATION FOR SEQ ID NO:12:

(i) SEQUENCE CHARACTERISTICS:
        (A) LENGTH: 101 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:12:

TCCAGACCTC CGAGTACTGC TGCACCACCG GCAAGTGCGG CCCCACCGAG TACTCCCGCT    60

TCTTCAAGCG CCTCTGCCCC GACGCCTTCT CCTACGTCCT C    101

(2) INFORMATION FOR SEQ ID NO:13:

(i) SEQUENCE CHARACTERISTICS:
        (A) LENGTH: 107 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:13:

GCTTGCCTGC AGTTATTATT AGGCGGTGGG GCAGAAGGTG ACGCGGTAGT TGGAGGAGCC      60

GGGGCAGGTG ACGGTGGTGG GCTTGTCGAG GACGTAGGAG AAGGCGT                    107

(2) INFORMATION FOR SEQ ID NO:14:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:14:

ACCCGGGGAT CCTCTCCATG GGACCTGCAG GCATGCA                                37

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:15:

CCGCTGCTCC TACACCGTCT GGGCCG                                            26

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:16:

TTAGGCGGTG GGGCAGAAGG                                                   20

(2) INFORMATION FOR SEQ ID NO:17:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:17:

AATTCTGCGG AACGTCGACC GCGACGGTGA CTGACACCTG GCGGCGAATG GATAAAGGG        60

(2) INFORMATION FOR SEQ ID NO:18:

-continued

```
    (i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:18:

CCCTTTTATC CATTCGCCGC CAGGTGTCAG TCACCGTCGC GGTCGACGTT CCGCAG         56

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Multicloning site of
            pTA18RN"

(xi) SEQUENCE DESCRIPTION: SEQ ID NO:19:

CCCGGGGATC CTCTCCATGG GACCTGCAGG CAT                                  33
```